United States Patent [19]
Hart

[11] Patent Number: 5,545,170
[45] Date of Patent: Aug. 13, 1996

[54] SURGICAL INSTRUMENT

[75] Inventor: Rickey D. Hart, Plainville, Mass.

[73] Assignee: Innovasive Devices, Inc., Marlborough, Mass.

[21] Appl. No.: 234,642

[22] Filed: Apr. 28, 1994

Related U.S. Application Data

[63] Continuation-in-part of Ser. No. 959,121, Oct. 9, 1992, Pat. No. 5,334,198.

[51] Int. Cl.$^6$ ............................................. A61B 17/00
[52] U.S. Cl. ...................... 606/148; 606/144; 606/139; 606/205
[58] Field of Search ........................... 606/41, 45–52, 606/205–208, 144–148, 139

[56] References Cited

U.S. PATENT DOCUMENTS

| | | | |
|---|---|---|---|
| 4,478,221 | 10/1984 | Heiss | 606/145 |
| 4,819,633 | 4/1989 | Bauer et al. | 606/52 |
| 5,196,023 | 3/1993 | Martin | 606/148 |
| 5,257,637 | 11/1993 | El Gazayerli | 606/148 |
| 5,318,579 | 6/1994 | Chow | 606/148 |
| 5,334,198 | 8/1994 | Hart et al. | 606/52 |

Primary Examiner—Angela D. Sykes
Assistant Examiner—Michael Peffley
Attorney, Agent, or Firm—Pandiscio & Pandiscio

[57] ABSTRACT

A surgical tool including a handle having a movable tool-operating member engaged therewith, a tool head having first and second members, and a coupling attaching the tool head to the handle. The first and second members of the tool head each include a cutting blade having a portion of a suture throw rundown tool extending distally therefrom. The cutting blades abut one another so as to act as a scissors when the first and second members are moved between open and closed positions. Further, the suture throw rundown tool portions mate with one another when the first and second members are in their closed position. The handle member also is adapted to rotate the inner shaft about its longitudinal axis. A method of using the surgical tool in the course of tying off lengths of suture extending from a surgical site also is provided.

26 Claims, 18 Drawing Sheets

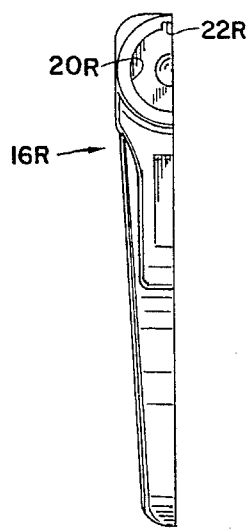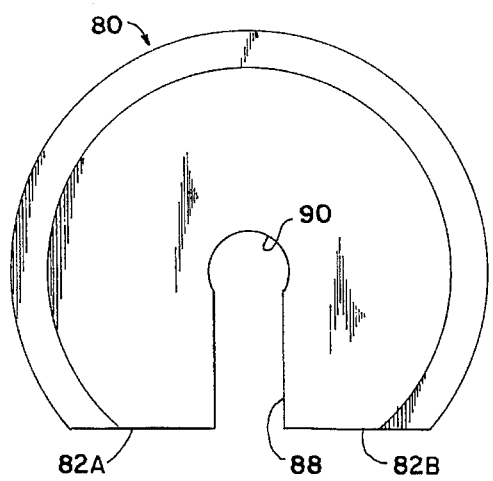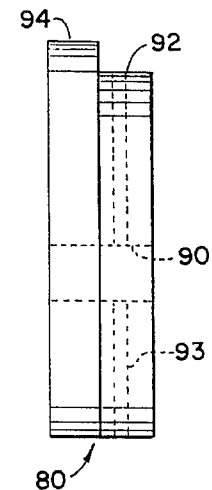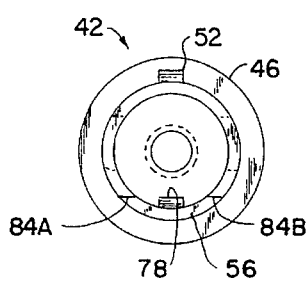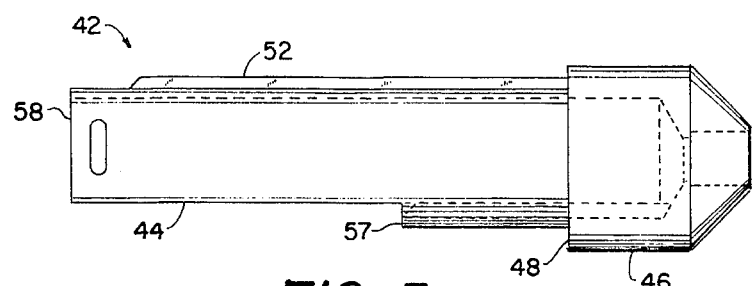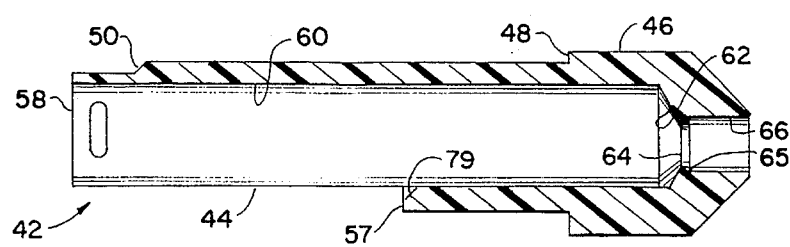

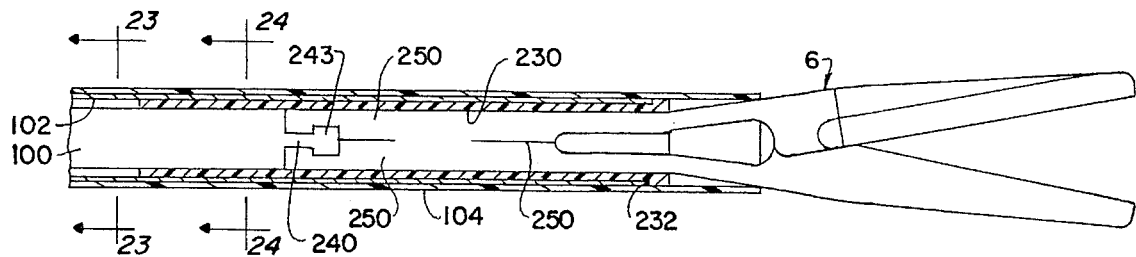
FIG. 22
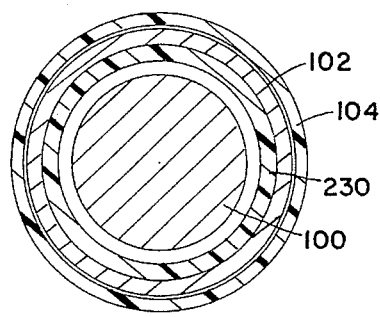
FIG. 24
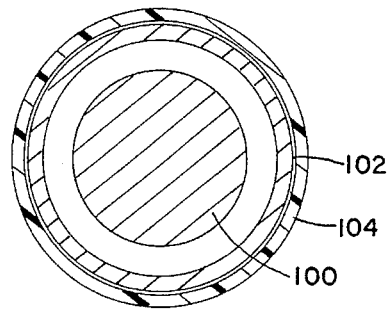
FIG. 23
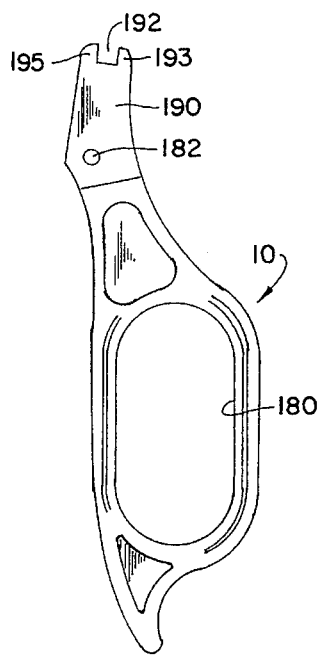
FIG. 25
FIG. 26
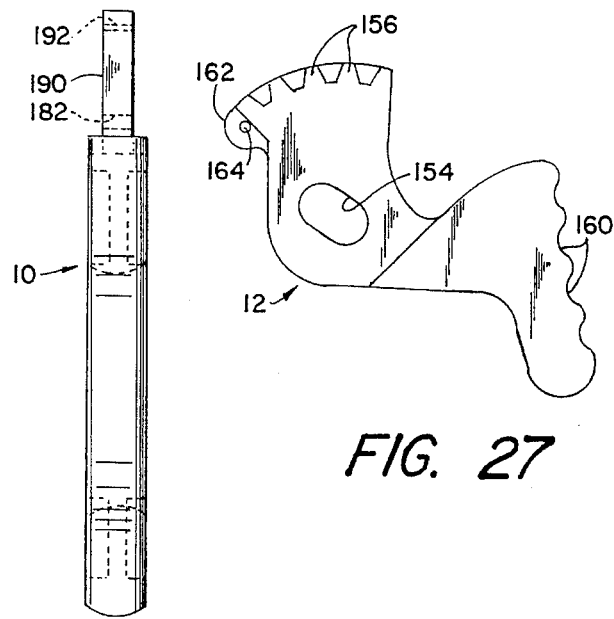
FIG. 27

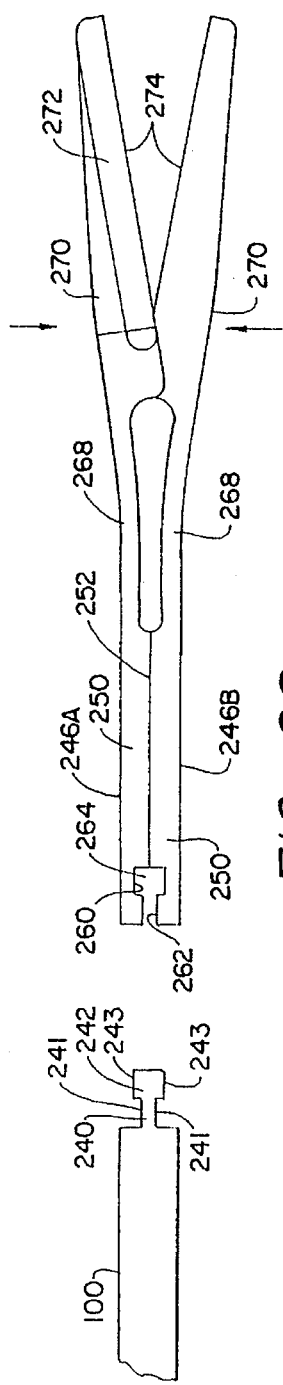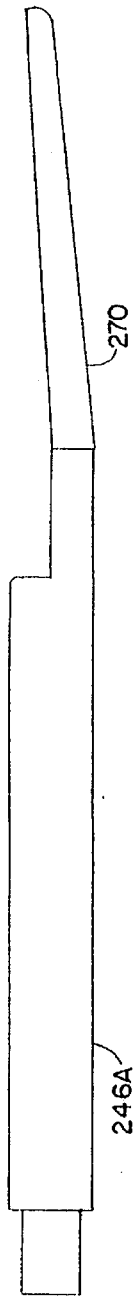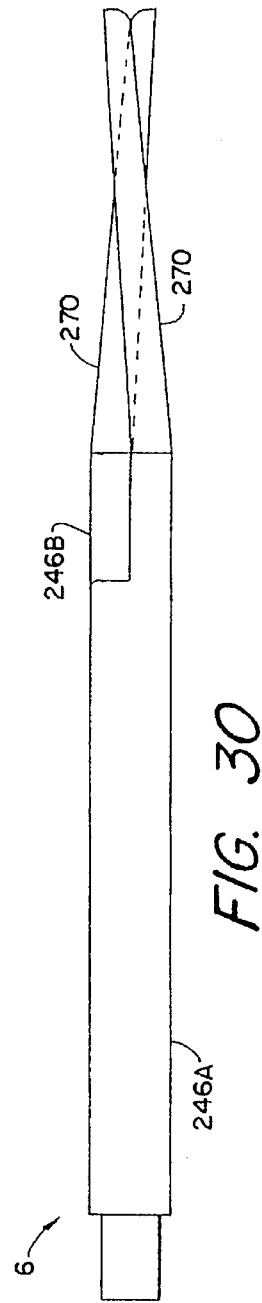

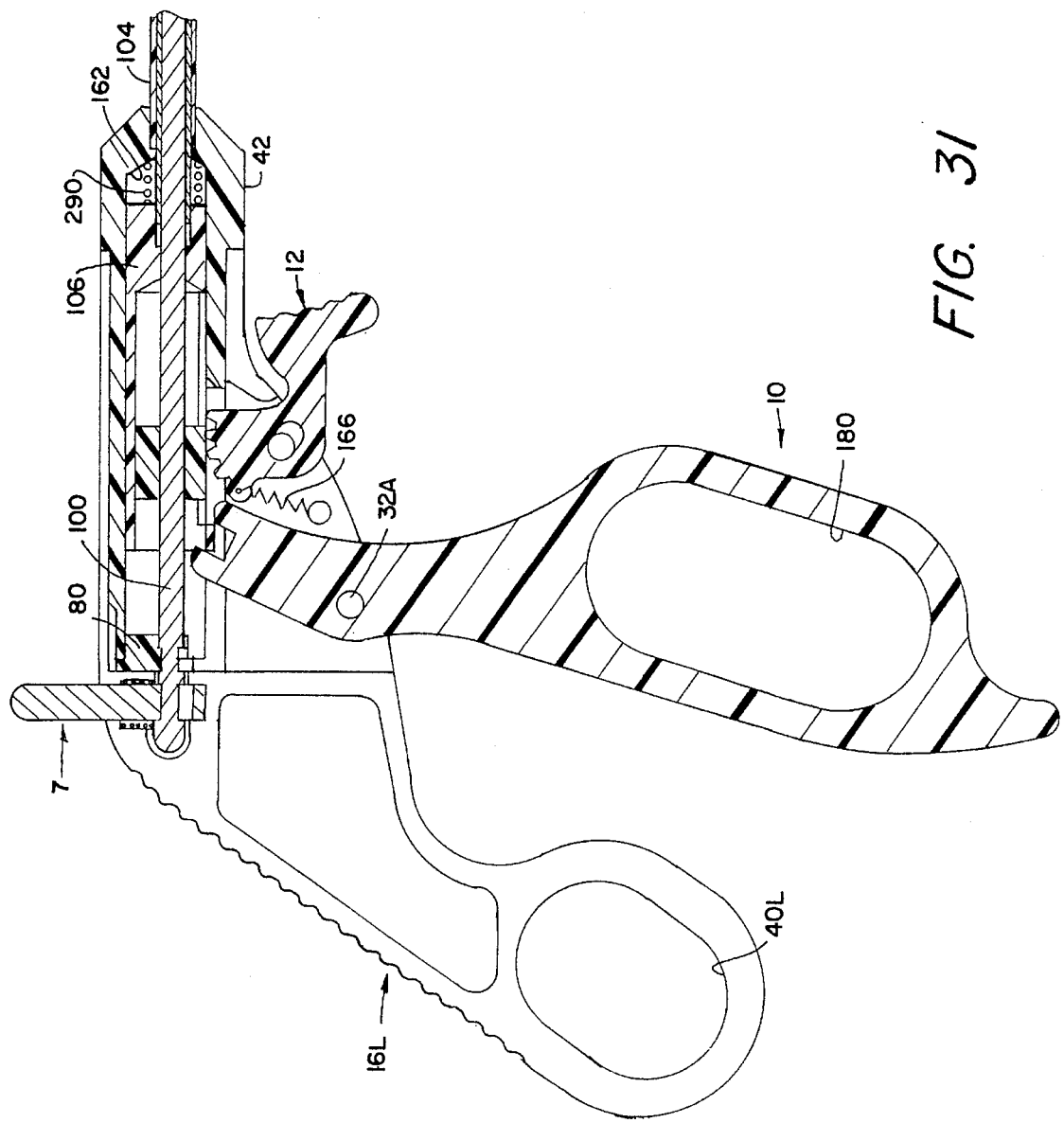

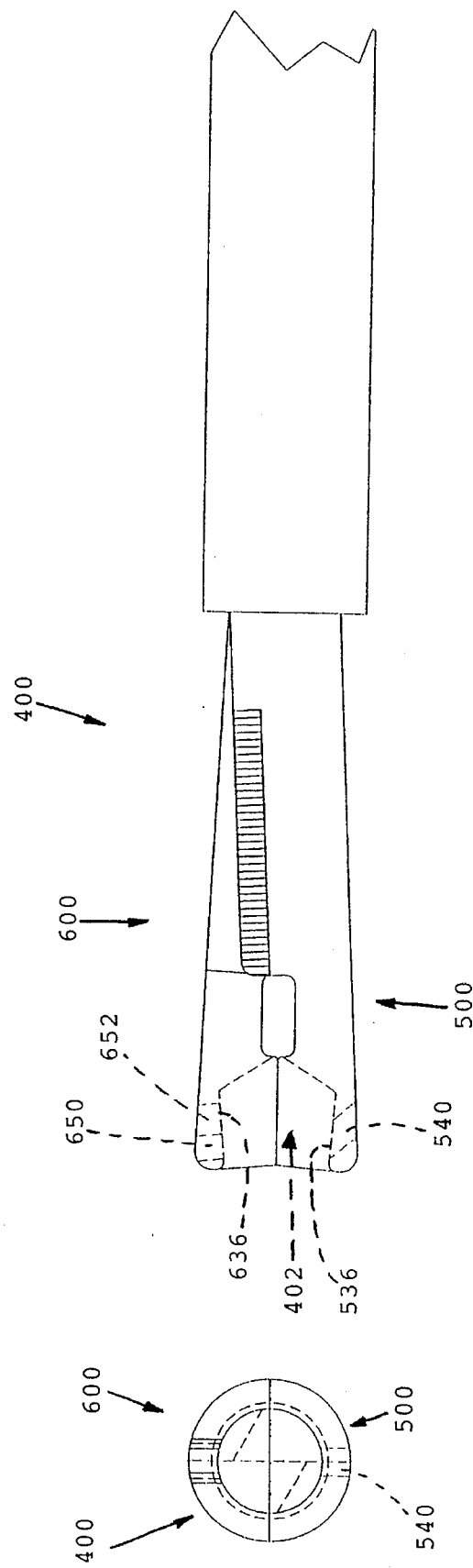

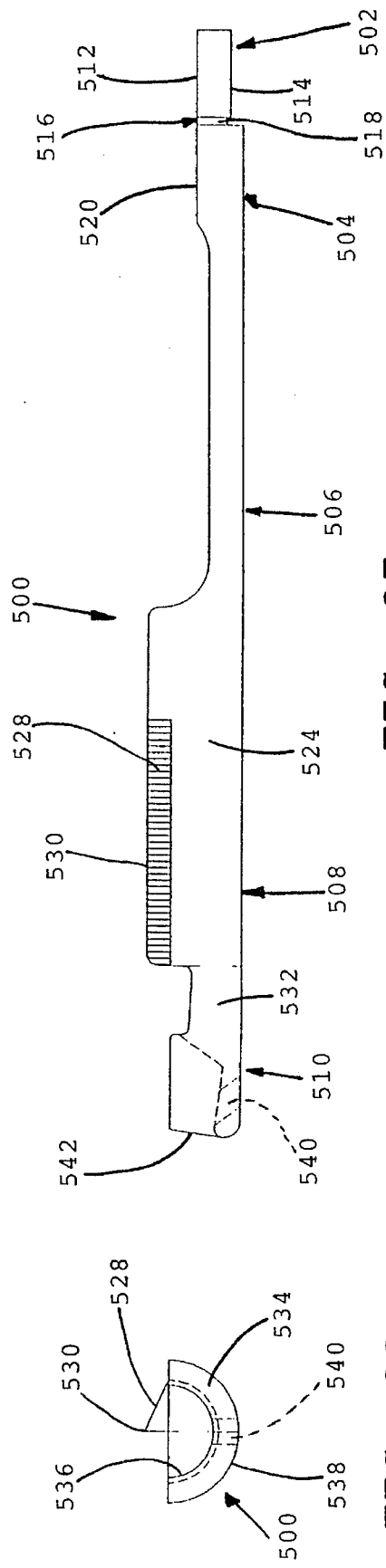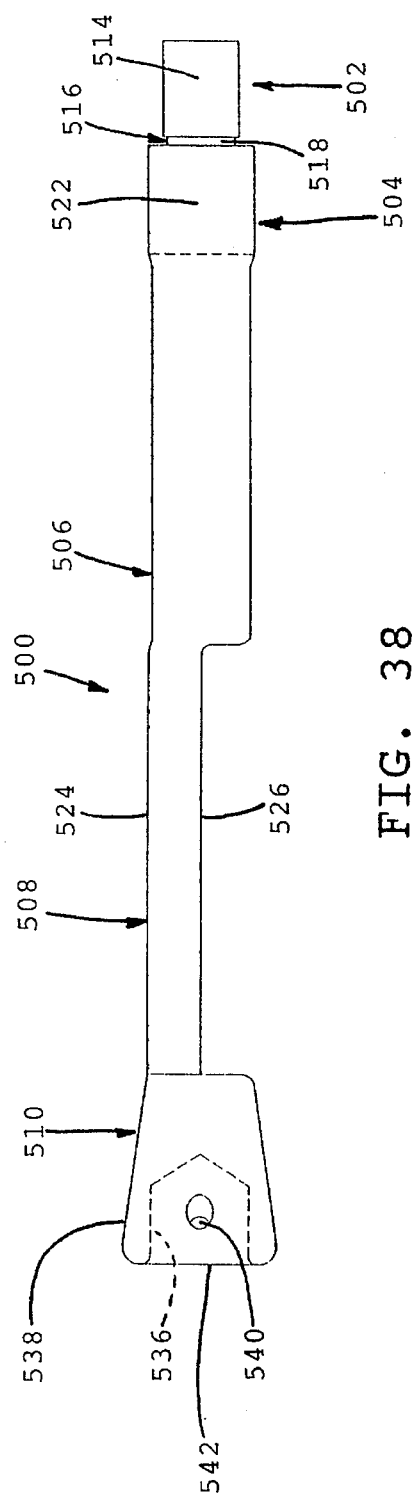
FIG. 37
FIG. 38
FIG. 39

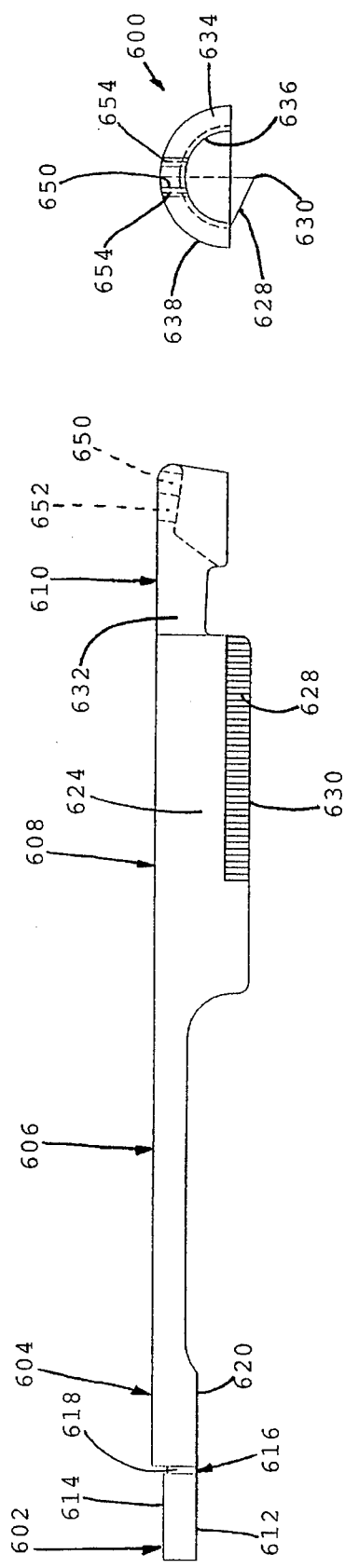
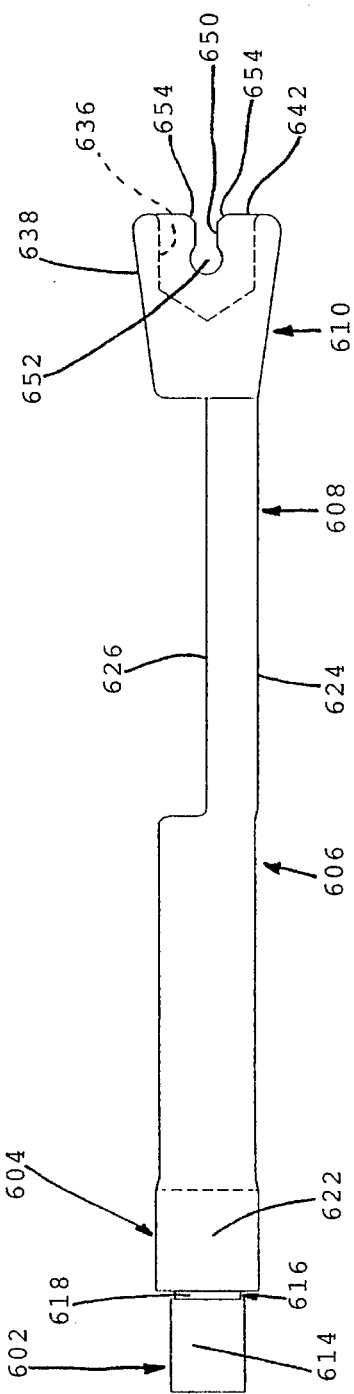
FIG. 42
FIG. 40
FIG. 41

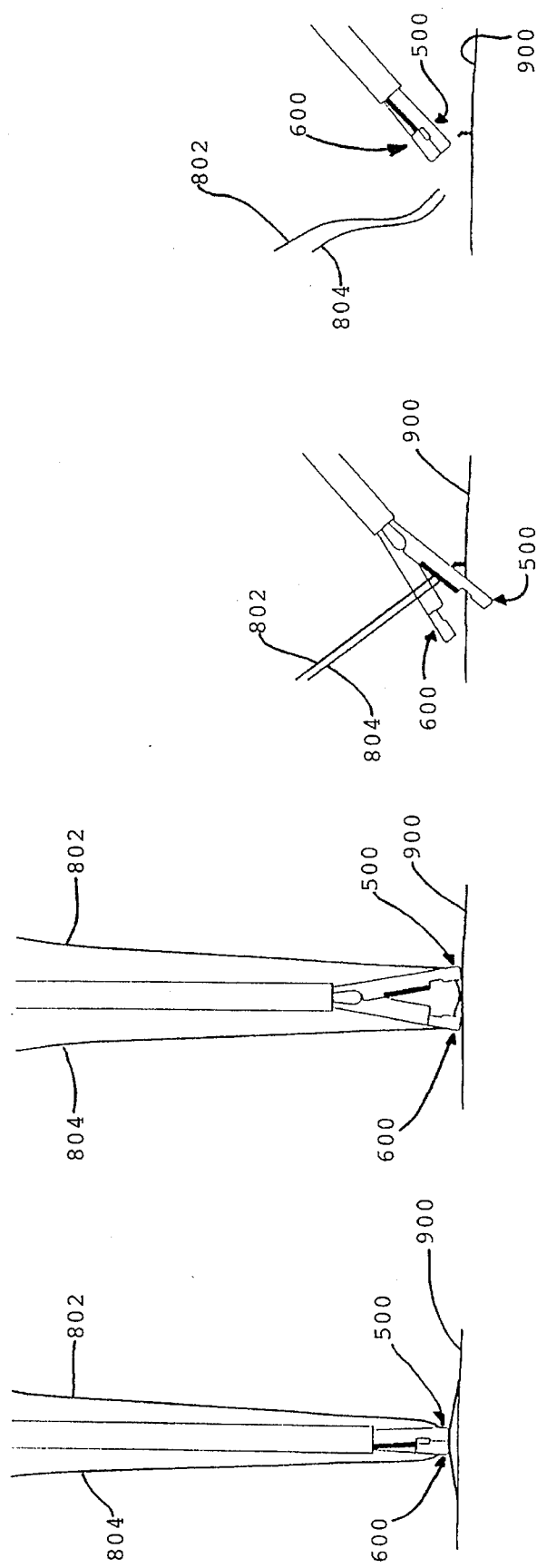

SURGICAL INSTRUMENT

This is a continuation-in-part of my prior U.S. patent application Ser. No. 07/959,121, filed Oct. 9, 1992, now U.S. Pat. No. 5,334,198, entitled "SURGICAL INSTRUMENT".

INTRODUCTION

This invention relates to surgical instruments and more particularly to instruments for use in endoscopic surgical procedures, including but not limited to laparoscopy.

BACKGROUND OF THE INVENTION

Human and animal surgery frequently requires the grasping, manipulating or cutting of tissue or other organic living matter at some distance from the surgeon's hands. In such cases endoscopic surgical methods are commonly employed that make it possible for skillful and precise surgery to be conducted despite the fact that the surgical site is a substantial number of inches from the point of initial incision in the person or animal being operated on. Endoscopic surgical procedures encompass both arthroscopic and laparoscopic surgery techniques. In endoscopic surgery, small incisions are made in the exterior surface of the person or animal being operated on, and the work being performed is observed by the operating surgeon by means of an optical device known as an endoscope which is inserted into the person or animal through a small incision. Endoscopic surgical techniques are displacing conventional open surgical techniques for many procedures, and hence there is a need for improved instruments for conducting such procedures.

A wide variety of surgical instruments have been devised for use in arthroscopic and laparoscopic surgical procedures, including instruments such as graspers, forceps and scissors for use in grasping, cutting or otherwise remotely manipulating bodily tissue and other matter during surgery.

A typical instrument employed in endoscopic surgery has a pair of articulated jaws, and a handle mechanism comprising two members, one movable with respect to the other, which can conveniently be manipulated so as to cause the jaws to open and close. Serrations, blades, cutting edges, or other features (depending upon the use for which the tool is intended) enable the jaws to perform various surgical functions, such as grasping or cutting. The articulated jaws are located at the distal end of a relatively long extension of the handle mechanism. The length of the extension is determined by the depth of the surgical site, while its cross-sectional dimensions are established by the maximum permissible incision size.

Many ingenious linkages have been devised for converting the surgeon's manual efforts at the handle end of the instrument into opening and closing of the tool's jaws. Most commonly, the surgical tool comprises a stationary handle member rigidly joined to a hollow outer shaft and a movable handle member pivotally attached to a coaxial inner shaft in the form of a tube or solid rod that is capable of reciprocal axial movement relative to the outer shaft, with the jaws being operatively coupled between the outer hollow shaft and the inner shaft member so as to open and close in accordance with relative axial movement of the outer and inner shafts. When the surgeon squeezes the stationary and movable handle members together, the outer and inner shafts coact in such a way as to make the jaws close. When the surgeon spreads the stationary and movable handle members apart, the motions are reversed and the jaws open. Publications illustrating the prior art include U.S. Pat. No. 3,404,677 and the prior art cited therein, as well as the following references: U.S. Pat. Nos. 4,836,205; 4,258,716; 4,084,594; 4,393,872; 5,026,375; 4,712,545; and 5,026,370.

OBJECTS AND SUMMARY OF INVENTION

A factor involved in the development of this invention is the realization that in the case of surgical scissors involving two telescoping shafts, having the outer hollow shaft fixed to the stationary handle member, in preference to it being movable and the inner shaft being fixed relative to the stationary handle member, is beneficial in that it avoids the possibility that apparent movement of the outer shaft when the instrument is operated would confuse the surgeon's depth perception in relation to the surgical site of the patient, thereby increasing the likelihood of surgical error.

Still other factors involved in development of this invention are the advantages derived from designing a surgical instrument with discrete subassemblies so as to facilitate (1) manufacture, (2) use of replaceable components, and (3) sterilization of selected components or subassemblies. Another factor considered in making the invention is the desirability of an instrument design that optionally includes a cauterization capability.

Accordingly, the primary object of this invention is to provide an improved surgical tool for use in endoscopic surgical procedures, e.g., laparoscopic surgery.

Another object of this invention is to provide an improved surgical instrument of the type described that is formed of a plurality of discrete subassemblies that facilitate manufacture and final assembly.

Still another object of this invention is to provide a surgical tool having a novel handle assembly.

A further object of this invention is to provide a surgical instrument or tool that comprises a tool head and means for electrifying said tool head so as to effect cauterization of tissue contacted by said tool head.

Still a further object is to provide a precision surgical instrument of the type described that is characterized by a removable scissors-type cutting head.

Another object of this invention is to provide a surgical instrument adapted for cutting tissue that does not confuse the surgeon into believing that the instrument is moving axially when it is operated without any intention on his part to move it axially.

A further object of this invention is to provide an improved surgical instrument of the type that has (1) a handle assembly and (2) a tool head coupled to and operated by the handle assembly that comprises co-operating jaws movable into and out of closing relation with one another, wherein the jaws are coupled to and operated by a coaxial arrangement of a rod secured to the handle assembly and a hollow shaft slidably surrounding the rod, the improved surgical instrument being characterized by means for concealing axial movement of the tube relative to the handle assembly.

A further specific object of this invention is to provide a surgical instrument characterized by a movable tube and a sheath that conceals axial movement of that tube.

Another specific object of the invention is to provide a surgical tool for use in various surgical procedures, including but not limited to endoscopic procedures for arthroscopy and laparoscopy, that comprises a handle and trigger assembly separably connected to an operating tool assembly that in turn comprises a hollow shaft and a rod telescopically mounted to one another, means for securing the rod to the handle assembly, and means connecting the hollow shaft to the trigger assembly whereby operation of the trigger will cause the shaft to move axially relative to the rod.

Another specific object of this invention is to provide a novel surgical instrument that is adapted for monopolar electrification, so as to permit cauterization at the surgical site.

Still another object of the present invention is to provide a surgical instrument having a novel tool head assembly adapted for suture throw rundown.

A specific object of the present invention is to provide a precision surgical instrument of the type just mentioned characterized by a scissors-type tool head wherein each cutting blade carries a portion of a surgical throw rundown assembly at its distal end, the respective portions of the surgical throw rundown assembly being adapted to substantially mate with one another when the cutting blades are located in their closed position.

Another specific object of the present invention is to provide a novel method for running a suture throw toward a surgical site.

A further specific object of the present invention is to provide a novel method for forming a knot substantially adjacent to a surgical site.

Still another specific object of the present invention is to provide a novel method for severing the suture ends extending from a knot which has been formed in accordance with the present invention.

The foregoing objects are obtained by providing a surgical instrument or tool that comprises a handle assembly having first and second handle members movably connected for movement relative to one another, an elongate rod releasably secured to the first handle member so as to form a fixed extension thereof, a tool head coupled to the rod having first and second members movable toward and away from one another, a tube (hollow shaft) coaxially and slidably surrounding the rod, with the tube having a first end slidably received in the handle assembly and a second end in position to be moved into and out of overlapping relation with said first and second members of said tool head, and drive means connecting said hollow tube and one of said handle members for causing said tube to shift axially relative to said rod between (1) a first retracted position when said one handle member is moved to a first position relative to the other handle member and (2) a second extended position when said one handle member is moved to a second position relative to said other handle member, said first and second members of said tool head being in a first open position relative to one another when said one handle member is in its said second position and being forced by said tube to close relative to one another when said one handle member is moved to its said first position. In a preferred embodiment of the invention, (1) the tool head is detachable from the aforementioned rod and replaceable by another like or different tool head; (2) the tool head is rotatable relative to the handle assembly; (3) the rod, tool head and hollow tube form a subassembly that is readily detachable from the handle assembly; and (4) the tool head may be electrified for monopolar cauterization.

In a preferred embodiment of the present invention, the instrument comprises a novel tool head that is designed to allow the surgical instrument to be used to tie off suture that is extending from a surgical site. The novel tool head includes means for running suture throws down the suture so as to form a knot adjacent to the surgical site, and means for thereafter severing the suture ends extending out of the knot.

One preferred method for tying off suture with the apparatus of the present invention includes the steps of:

(1) forming a surgical throw in the suture ends extending away from a surgical site;

(2) with the surgical instrument's tube in a first position, threading one of the suture ends through a first opening in the surgical instrument;

(3) sliding the other suture end through a second opening in the surgical instrument, and moving the surgical instrument's tube to a second position;

(4) while holding the suture ends taut, running the surgical throw toward the surgical site with the surgical instrument;

(5) moving the surgical instrument's tube back to its first position, thereby pulling the surgical throw tight;

(6) disengaging the two suture ends from the surgical instrument;

(7) repeating steps 1–6 as many times as necessary so as to form the desired surgical knot;

(8) with the surgical instrument's tube in its first position, positioning the surgical instrument adjacent to the suture ends extending away from the surgical knot; and (9) moving the tube from its first position to its second position so as to sever the suture ends extending out of the knot.

Other necessary and optional features are disclosed by or rendered obvious by the following detailed description which is to be considered together with the accompanying drawings.

THE DRAWINGS

FIG. 4 is a front view in elevation of the handle part shown in FIG. 3;

FIG. 5 is a side elevation of the insulator housing;

FIG. 6 is a sectional view in side elevation of the insulator housing taken along its center line;

FIG. 7 is a rear end view of the insulator housing;

FIG. 8 is a front end view in elevation of a cap for the insulator housing;

FIG. 9 is a side view in elevation of the end cap of FIG. 8;

FIG. 22 is an enlarged cross-sectional view of a portion of the tool head drive assembly;

FIG. 23 is a cross-sectional view taken along line 23—23 of FIG. 22;

FIG. 24 is a cross-sectional view taken along line 24—24 of FIG. 22;

FIG. 25 is a side elevation of the operating trigger member;

FIG. 26 is a front end view in elevation of the trigger member of FIG. 25;

FIG. 27 is a side view in elevation of the rotational trigger member;

FIG. 28 is an exploded view showing how the tool head is detachable from its supporting rod;

FIG. 29 is a top plan view of one of the scissors blade members;

FIG. 30 is a top plan view of the tool (scissors) head in open position;

FIG. 31 is a fragmentary sectional view showing inclusion of a spring for holding the trigger member in its forward position;

FIG. 35 is an enlarged side view, partially cut away, showing the novel tool head of FIG. 32 in its closed position and with the internal structure of the surgical throw rundown assembly shown in phantom;

FIG. 36 is a distal end view of the novel tool head of FIG. 35;

FIG. 37 is a side elevational view of the lower one of the two tool head members shown in FIG. 33, with the member being shown at an intermediate stage of manufacture before it has been bent into the shape shown in FIG. 33;

FIG. 38 is a bottom view of the tool head member shown in FIG. 37;

FIG. 39 is a distal end view of the tool head member shown in FIG. 37;

FIG. 40 is a side elevational view of the upper one of the two tool head members shown in FIG. 33, with the member being shown at an intermediate stage of manufacture before it has been bent into the shape shown in FIG. 33;

FIG. 41 is a top view of the tool head member shown in FIG. 40;

FIG. 42 is a distal end view of the tool head member shown in FIG. 40;

FIG. 46 is a view similar to that of FIG. 45, but showing the novel tool head having run the surgical throw down to the surgical site;

FIG. 47 is a view similar to that of FIG. 46, but showing the two tool head members in their open position;

FIG. 48 is a view similar to that of FIG. 47, but showing the novel tool head about to cut off the suture ends extending away from a knot which has been formed at the surgical site; and FIG. 49 is a view similar to that of FIG. 48, but showing the novel tool head after cutting of the suture ends extending away from the knot formed at the surgical site.

It is to be understood that some of the several views presented by the drawings are drawn to different scales for ease of illustration and description. Also, like parts and features are identified by like numerals in the drawings.

PREFERRED EMBODIMENT OF INVENTION

Figure 1:
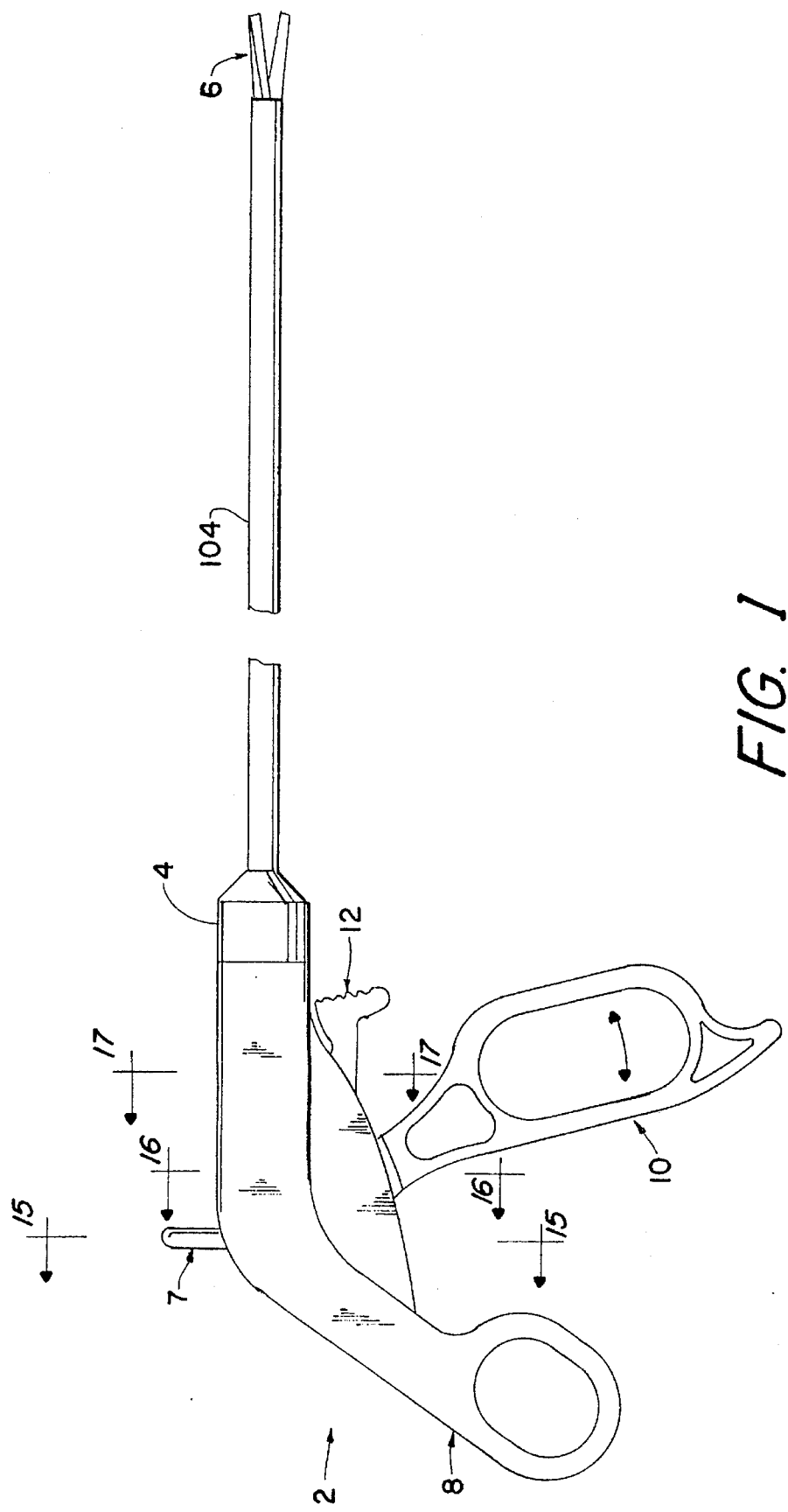
FIG. 1 is a side elevation of a preferred embodiment of the invention constituting a surgical scissors designed for laparoscopic surgery.

Referring now to FIG. 1, there is shown a surgical instrument which, in its preferred form, is a scissors designed for laparoscopic procedures. The instrument comprises a handle assembly 2, a drive assembly 4, a tool head 6 in the form of a scissors head, and an electrical terminal pin 7. The handle assembly may take various forms. In this preferred embodiment of the invention, the handle assembly comprises a fixed or stationary handle 8, a movable handle member in the form of a trigger 10 for operating the scissors head, and a rotation trigger member 12 which cooperates with the drive means carried by the handle assembly to effect controlled rotation of the scissors head relative to the handle assembly.

Figure 2:
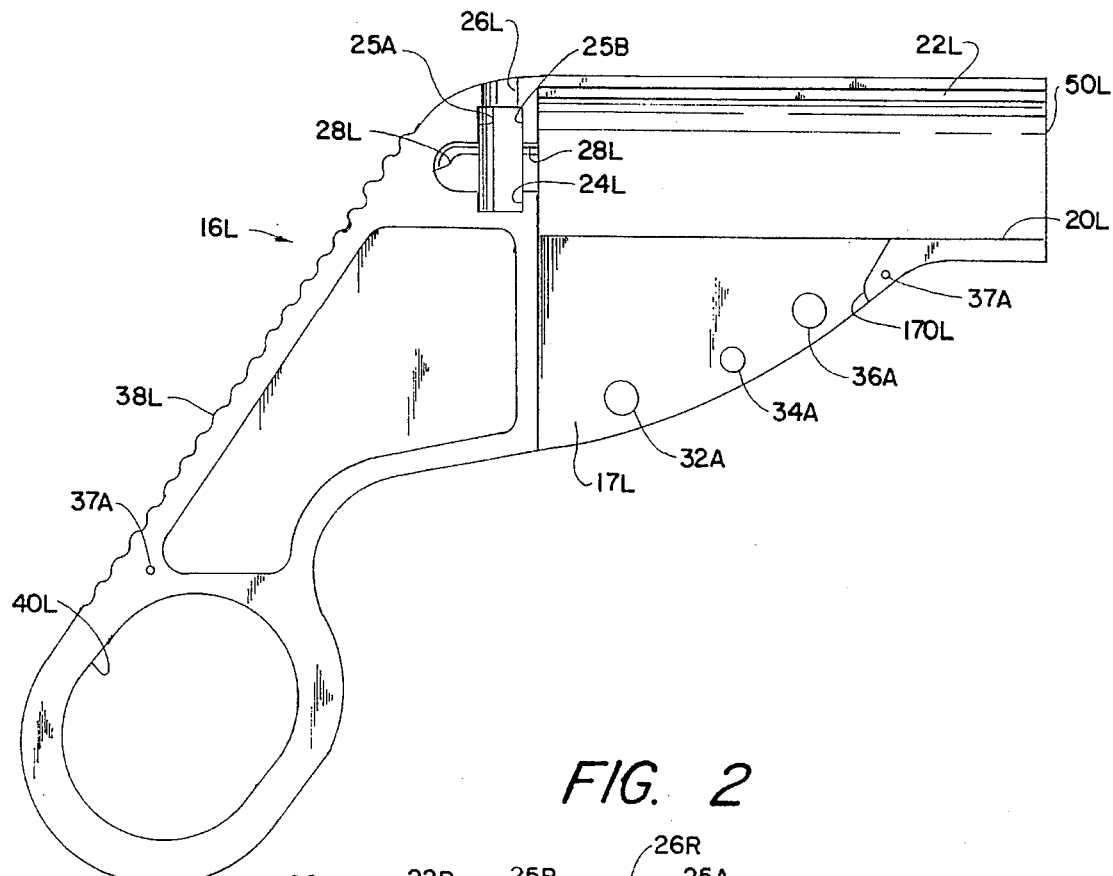
FIG. 2 is a side view in elevation of the left hand half of the handle housing.
Figure 3:
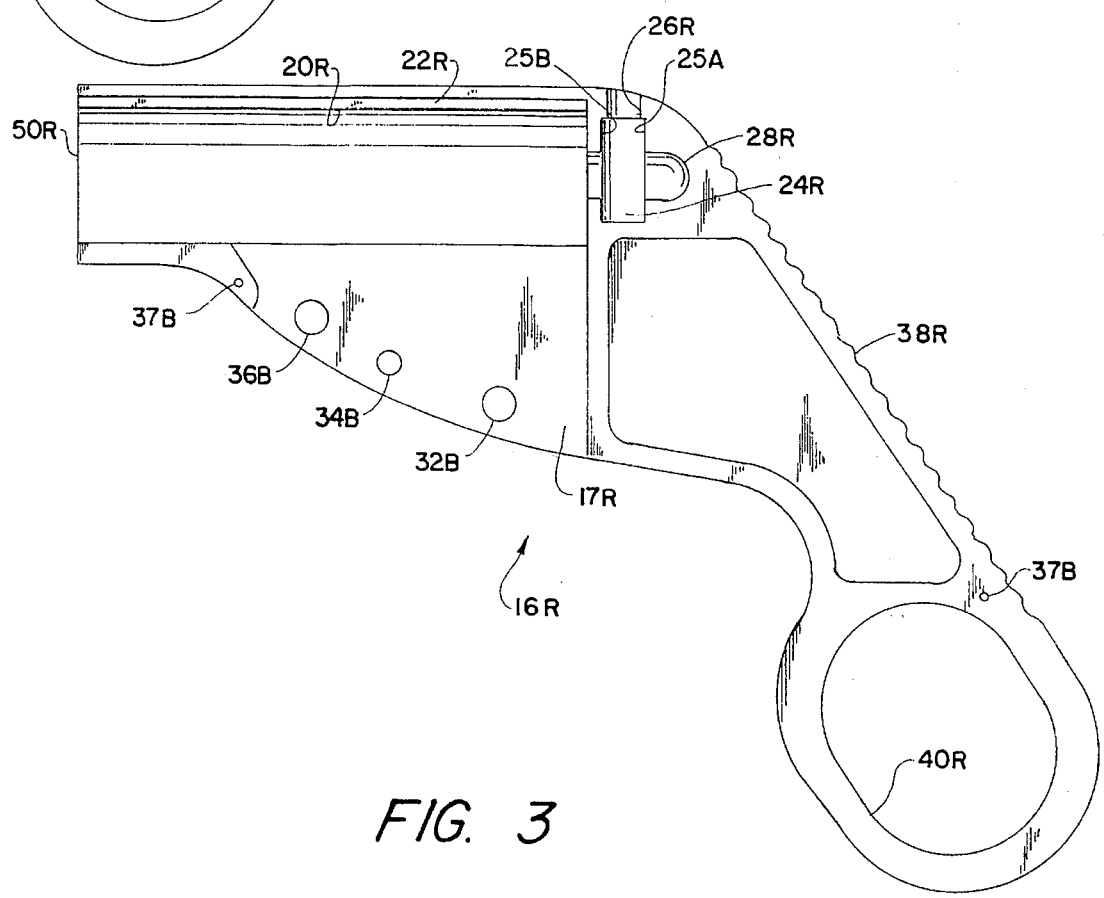
FIG. 3 is a side view in elevation of the right hand half of the handle housing.

Looking now at FIGS. 2–4, the fixed handle 8 comprises complementary left-hand and right-hand handpieces 16L and 16R that preferably are made of a plastic material such as a polysulfone or polycarbonate. These handpieces are complementary in the sense that they are mating halves of member 8 and, except as otherwise stated hereinafter, handpieces 16L and 16R are identical mirror images of one another. Handpieces 16L and 16R have like circularly curved axially-extending elongate cavities 20L and 20R respectively on their mutually confronting sides. Additionally, handpieces 16L and 16R have axially-extending flat-sided grooves 22L and 22R that intersect cavities 20L and 20R respectively at the twelve o'clock position (FIG. 4). Grooves 22L and 22R cooperate to define a keyway for an insulator housing 42 (FIGS. 5–7) described hereinafter that forms part of the drive assembly 4. Handpieces 16L and 16R also have semi-circular cavities 24L and 24R that communicate with reduced-diameter semi-circular cavities 26L and 26R respectively. Intersecting the cavities 24L and 24R are additional semi-circular cavities 28L and 28R which also intersect the cavities 20L and 20R, respectively, at right angles. Cavities 20L, 20R, 24L, 24R, 26L, 26R, 28L and 28R are semi-circular in the sense that they have a semi-cylindrical cross-section. The left handpiece 16L is provided with three projections or pins 32A, 34A and 36A of circular cross-section that are sized to make a close fit in like-spaced cavities or depressions 32B, 34B and 36B in the right handpiece 16R. Although provided for other purposes hereinafter described, pins 32A, 34A and 36A serve incidentally as assembly registration pins for handpieces 16L and 16R.

Preferably, but not necessarily, one handpiece (16L) has two or more locating pins 37A that are sized and located so as to mate closely with shallow depressions or cavities 37B in the other handpiece (16R), so as to facilitate and assure proper registration of the two handpieces when they are engaged with one another in forming handle 8. Handpieces 16L and 16R are secured together, preferably by a suitable cement such as an epoxy resin or by ultrasonic welding.

For reasons of convenience of use by the surgeon, it is preferred, but not essential, that the rear surface of the left and right handpieces have a knurled configuration as shown at 38L and 38R, respectively, so as to facilitate gripping of the handle unit. Additionally, it is preferred, but not essential, that the handpieces be provided with complementary finger holes 40L and 40R for receiving the thumb of the surgeon.

Drive assembly 4 comprises an insulator housing 42 and a tube housing 106 (see FIG. 10 and FIGS. 5–7 and 18–21), plus components (other than tool head 6) that are attached to housings 42 and 106.

Cavities 20L and 20R in the two handpieces cooperate to form a cylindrical chamber for receiving insulator housing 42. The latter, which preferably is made of the same material as handpieces 16, comprises a cylindrically shaped elongate section 44 having a peripheral flange 46 at its forward or distal end so as to provide a shoulder 48 that engages the forward end surfaces 50L and 50R of the left and right handpieces. Tubular section 44 is formed with an external longitudinally-extending rectangular rib 52 at the twelve o'clock position (as viewed in FIG. 7) that is sized to make a close sliding fit in the keyway formed by grooves 22L and 22R of the left and right handpieces 16L and 16R respectively. In addition, tubular section 44 has an axially-extending slot 56 (FIG. 7) formed symmetrically about the six o'clock position (as viewed in FIG. 7) that serves as an access hole for portions of trigger members 10 and 12 and a slide hole for a portion of tube housing 106. As viewed in FIG. 7, slot 56 terminates in side edge surfaces 84A and 84B. The circumference of section 44 in the portion having slot 56, i.e., the circumference measured between the outer edges of side edge surfaces 84A and 84B, measures about 260°, so that slot 56 extends through an angle of about 100° (50° on either side of the six o'clock position). As viewed in FIGS. 5–7, slot 56 starts at the proximal (rear) end of section 44 and ends close to the midpoint of housing 42, leaving an arcuate end surface or shoulder 57 (FIG. 6).

Insulator housing 42 has a center bore 60 which is of constant diameter throughout its length, except that (1) at its distal (front) end it is tapered as shown at 62 and then communicates in turn with a smaller diameter hole 64 and a bore 66 that has a slightly larger diameter than hole 64 so as to form an annular shoulder 65, and (2) it is formed with an internal rectangular axially-extending rib 78 at the six o'clock position (as seen in FIG. 7). Preferably the proximal (rear) end of rib 78 is bevelled as shown at 79. Affixed to the proximal (rear) end of the insulator housing 42 is an end cap 80 (FIGS. 8 and 9) that preferably is made of the same material as handpieces 16. End cap 80 is generally circular in cross-section except that its circumference is less than a full 360°, so as to provide flat bottom surfaces 82A and 82B. Preferably its circumference, measured between the outer edges of surfaces 82A and 82B (as viewed in FIG. 8) measures about 240°. Consequently when cap 80 is applied to housing 42 so that its surfaces 82A and 82B extend parallel to bottom edge surfaces 84A and 84B, a portion of the rear end surface 58 of housing 42 in the region of the six o'clock position is not covered by cap 80, so as to allow clearance between the cap and trigger 10 when it is desired to pull the drive assembly out of the handle assembly.

Cap 80 is provided with a radially-extending through slot 88 that terminates at the center of the cap with a circularly curved hole 90 that is concentric with the center axis of the cap. Also cap 80 comprises a reduced diameter body section 92 and a peripheral flange 94. Body section 92 is sized to make a close fit in the proximal end of the insulator housing, with flange 94 having the same o.d. as tubular section 44. The cap is ultrasonically welded or cemented, e.g., by an epoxy resin, to the proximal end surface 58 of housing 42, with the circularly curved hole 90 being concentric with the hole 64 of housing 42.

Figure 10:
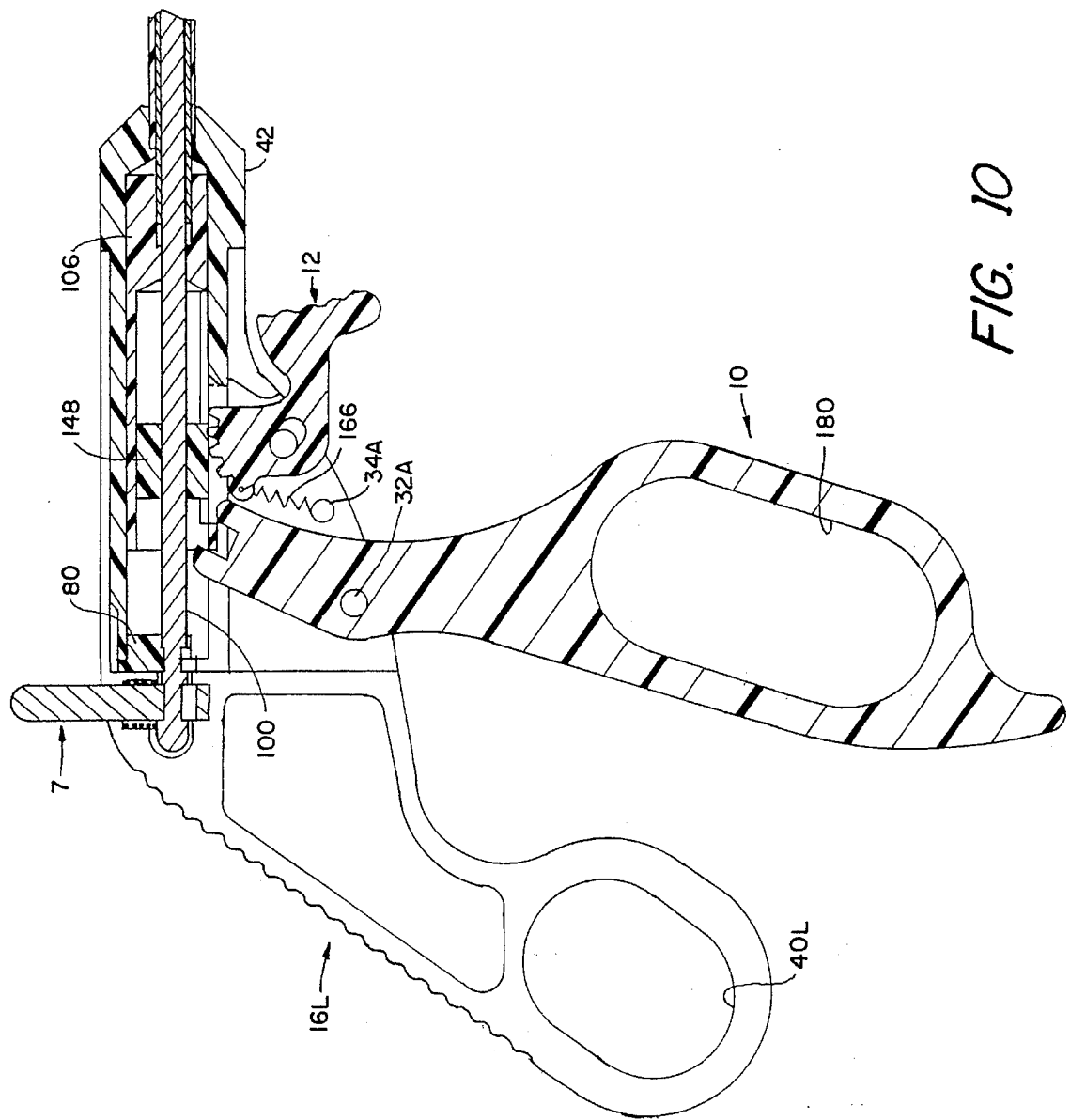
FIG. 10 is a fragmentary longitudinal sectional view in side elevation showing the handle assembly without the right hand half of the handle housing.

AS shown in FIG. 10, insulator housing 42 is disposed in the cylindrical chamber formed by the mating cavities 20L and 20R of handpieces 16, with shoulder 48 engaging the forward end surfaces 50L and 50R of those handpieces and rib 50 being disposed in the keyway formed by grooves 22L and 22R. The interlocking of rib 52 with the keyway formed by grooves 22L and 22R serves to dictate orientation of housing 42 relative to the handle assembly. Housing 42 is releasably secured in handle assembly 2 by a locking action between a terminal pin 7 and rod 100 as hereinafter described.

Referring now to FIGS. 10–14 and 18–27, drive assembly 4 comprises, in addition to insulator housing 42, the following elements: a support rod 100 for tool head 6, an outer operating tube or sleeve 102, an outer sheath in the form of a tube 104, and a tube housing 106. The outer sheath 104 is cylindrical and its proximal (rear) end extends into axial bore 66 in engagement with shoulder 65 and is fixed to the insulator housing by a press fit or in some other suitable way, e.g., by an epoxy cement, as permitted by the materials being secured together. In this preferred embodiment, sheath 104 is made of a suitable electrically insulating material, e.g., a fluorinated hydrocarbon such as Teflon, while tube 102 may be made of an electrically-conductive metal or a conductive plastic. Tube 102 has an outer diameter sized so that it makes a close sliding fit within outer sheath 104 and also in the reduced diameter hole 64.

Figure 19:
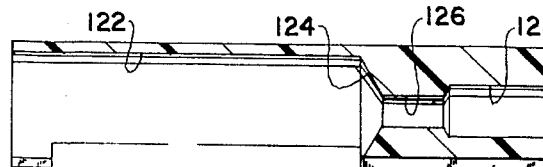
FIG. 19 is a longitudinal sectional view in elevation of the tube housing.
Figure 20:
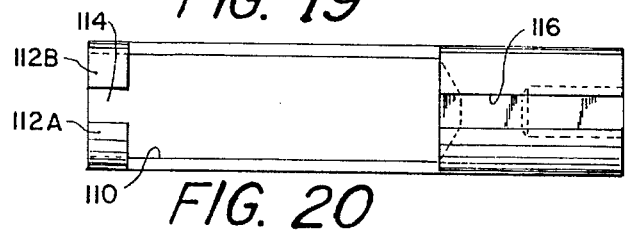
FIG. 20 is a bottom plan view of the tube housing.

Referring now to FIGS. 18–21, tube housing 106 preferably is made of a lubricious plastic material, e.g., molded DELRIN. Housing 106 is a hollow member formed with a rectangular aperture 110 that is centered about the six o'clock position and extends through about 100° of its circumference. Aperture 110 is located just short of the proximal or rear end of the tube housing, so as to form a depending lug section 112 which serves as part of the pivotal connection for the trigger member 10. Housing 106 also is provided with an axially-extending slot 114 that intersects aperture 110 and splits the lug section 112 into two like parts 112A and 112B (FIG. 20). Additionally, housing 106 has an external axially-extending shallow groove 116 located at approximately the six o'clock position. Groove 116 is aligned with and has substantially the same width as slot 114. Groove 116 slidably mates with the elongate rib 78 on the inner surface of insulator housing 42. The sliding interengagement of groove 116 with rib 78 prevents the tube housing from rotating relative to insulator housing 42 and also aligns aperture 110 with slot 56.

Referring now to FIG. 19, the axial bore of tube housing 106 is characterized by a first relatively large diameter section 122, a tapered section 124, a relatively small intermediate section 126 and an intermediate diameter size section 128. Axial bore section 126 is sized to make a close sliding fit with support 100. The intermediate size bore section 128 is sized so as to tightly accommodate the proximal (rear) end of tube 102. The latter is fixed to tube housing 106 by a press fit or by other suitable means, e.g., by a cement or by soldering, brazing or welding as is deemed practical according to the materials being joined.

Figure 11:
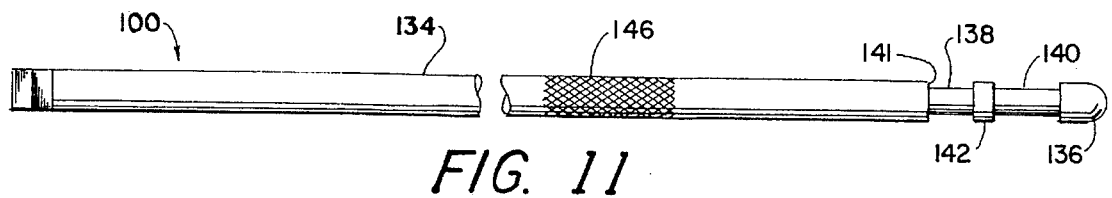
FIG. 11 is a plan view of a rod to which the tool head is connected.
Figure 12:
FIG. 12 is a side view showing the rod of FIG. 11 rotated 90° on its axis.
Figure 13:
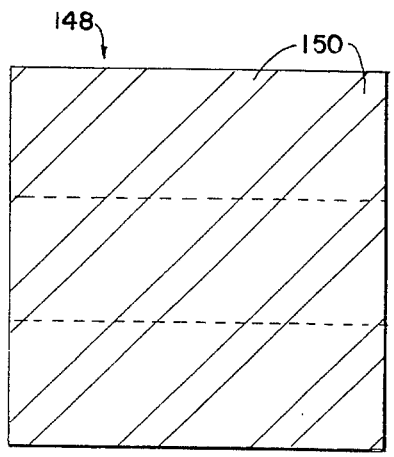
FIG. 13 is a side view of a helical gear that is affixed to the rod of FIG. 11.
Figure 14:
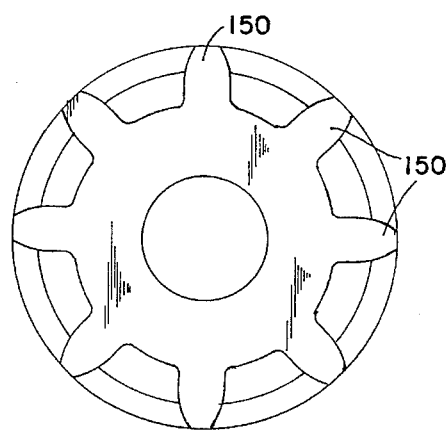
FIG. 14 is an end view of the gear of FIG. 13.
Figure 21:
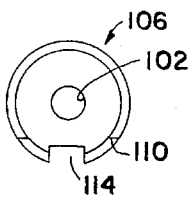
FIG. 21 is a front end view of the tube housing.
Figure 18:
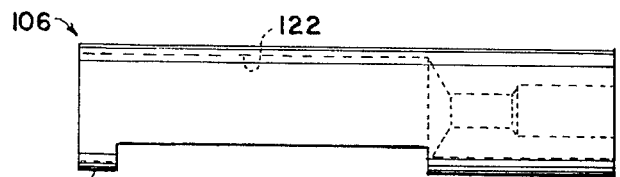
FIG. 18 is a side view in elevation of the tube housing.

Referring now to FIGS. 11 and 12, for the majority of its length, rod 100 has a constant relatively large size diameter as shown at 134. The proximal end of rod 100 is provided with a rounded head section 136 which is sized to make a close fit in the rounded rear end of the chamber formed by the mating cavities 28L and 28R. Intermediate sections 134 and 136 the rod has two reduced diameter sections 138 and 140 that are separated by an intermediate flange section 142 which preferably has a diameter close to that of rod section 134. An annular shoulder 141 is formed by the rod at its section 138. The opposite or distal end of rod 100 is formed so as to accommodate the tool head 6. Further details of the construction of the forward or distal end of support rod 100 are presented hereinafter.

The proximal (rear) end of rod 100 slidably extends through the bore section 126 of tube housing 106 and its intermediate or reduced diameter section 138 is accommodated by and makes a close fit in the circularly curved center hole 90 of cap 80. The radius of the hole 90 of cap 80 is smaller than the radius of the flange section 142 of the drive rod, while the length of rod section 138 is only slightly greater than the overall thickness of cap 80. As a result, shoulder 141 and flange 142 engage opposite sides of cap 80, thereby preventing rod 100 from moving axially relative to cap 80, and vice versa. Hence, if rod 100 is inserted into tube housing 106 and tube 102, and that resulting subassembly is then inserted into the insulator housing via its open end, and thereafter the reduced diameter plug section 92 of cap 80 is secured in the circularly curved section 44 of the insulator housing 42, rod 100 will be fixed relative to the insulator housing while tube housing 106 and tube 102 will be free to move axially relative to the rod and the insulator housing to the extent permitted by the difference in the length of tube housing 106 and the distance between end cap 80 and the junction of bore sections 60 and 62.

Figure 17:
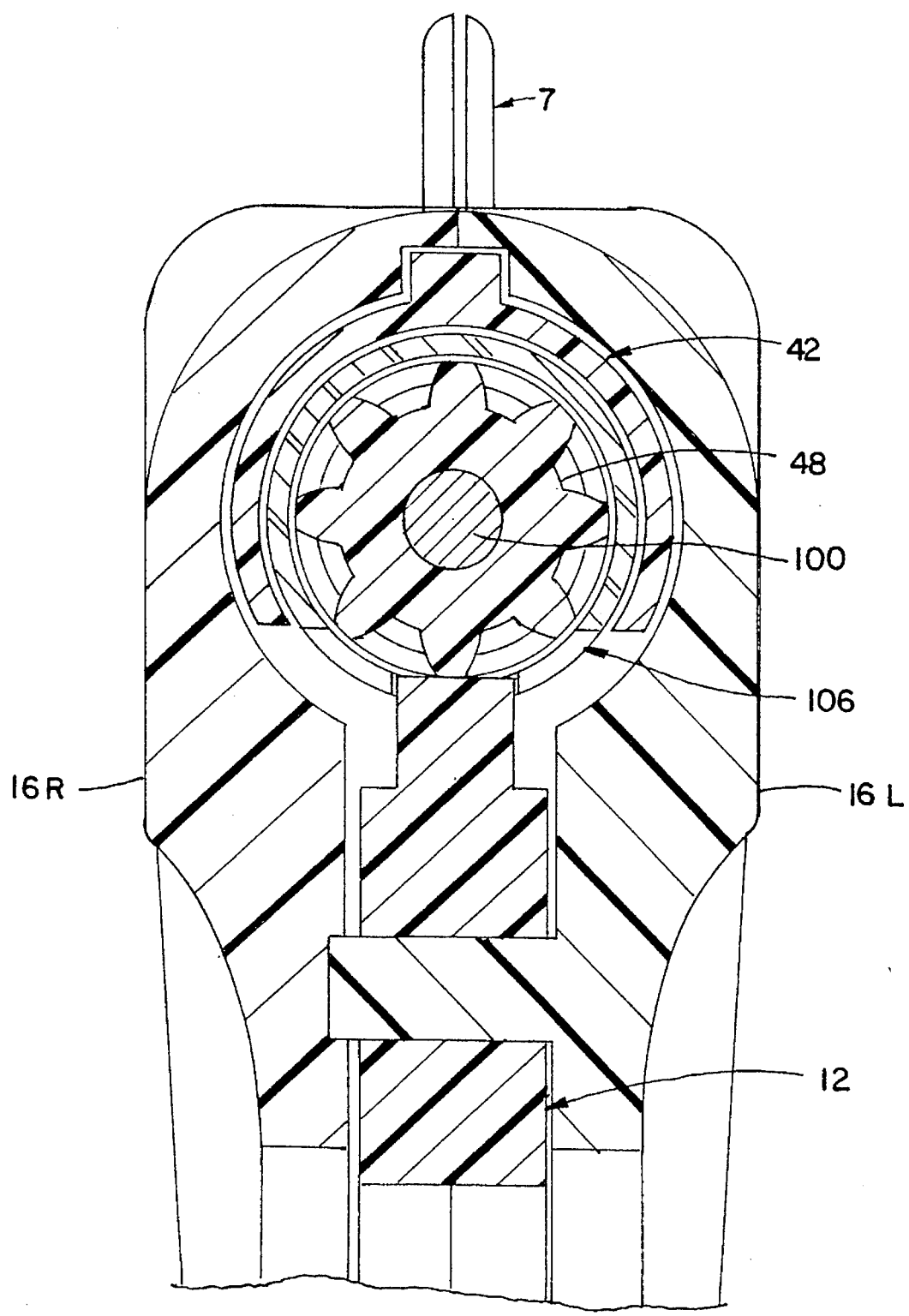
FIG. 17 is a cross-sectional view taken along line 17—17 of FIG. 1.

Looking now at FIGS. 10–14 and 17, rod 100 has a knurled section 146 which is slightly larger in diameter than its section 134 and is sized to accommodate a helical gear 148 having a center hole 149. The latter may be affixed to rod 100 by a press fit with knurled surface 146, or by means of a suitable cement or other fixing agent, e.g., an epoxy cement. Gear 148 may be made of a metal or a plastic. Rod 100 is preferably made of metal for electrical conduction purposes. The preferred mode of mounting helical gear 148 to the drive rod is by way of a friction fit, augmented by a suitable cement. Gear 148 has evenly shaped, helically-directed gear teeth 150. Gear 148 is sized so that a portion of its periphery projects through aperture 110 in tube housing 106 for engagement of its teeth 150 by the rotation trigger member 12 (FIGS. 10, 17 and 27).

Trigger member 12 has an elongate hole 154 for accommodating pivot pin 36A. Additionally, one end of that rotation trigger is provided with a plurality of helically pitched teeth 156 which are shaped and sized to mate with teeth 150 of gear 148. The opposite end of the trigger member is preferably knurled or formed with grooves 160 to eliminate slippage between the rotation trigger member and the surgeon's finger used to operate that trigger member. Trigger member 12 also has an extension 162 provided with a small aperture 164 which is sized to accommodate one end of a tension spring 166. The opposite end of the spring is formed with a circular extension sized to fit over pin 34A of the left handpiece 16L. Pivot hole 154 is elongated so as to facilitate operation of the rotation trigger. When the latter is mounted to pin 36A, spring 166 exerts a force that normally holds the rotation trigger in its forward and down position (FIG. 10), with its teeth 156 being out of engagement with gear 148. When that trigger is pulled back by a finger of the operating surgeon, its moves upwardly on pivot pin 36A and also rotates on that pin, causing its teeth 156 to engage and rotate helical gear 144, thereby causing rotation of drive rod 100. Rotation of trigger 12 is limited in one direction by its engagement with the surface 57 defining the forward end of slot 56 of the insulator housing 42, and in the other direction by its engagement with shoulders 170L and 170R (FIGS. 2 and 3) formed by handpieces 16L and 16R.

Referring now to FIGS. 10, 16, 25 and 26, trigger member 10 is preferably formed with an elongate aperture 180 to accommodate a finger of the surgeon. Additionally, the trigger member has a hole 182 to accommodate pivot pin 32A on the left handpiece. The trigger member has a reduced thickness end portion 190 that is provided with a rectangular notch 192 that subdivides its upper end into two fingers 193 and 195. The notch and fingers are sized so as to make a pivotal connection with lug 112 of tube housing 106. It is to be noted that handpieces 16L and 16R have recesses 17L and 17R to accommodate the reduced thickness end portion 190 of the trigger member. Trigger member 10 is pivotally mounted so that its notch 192 is engaged with lug 112. Pivotal movement of trigger 10 causes axial movement of tube housing 106 and tube 104 when the trigger member is pivoted toward and away from stationary handle 8. Pivotal movement of trigger 10 relative to the stationary handle 8 is illustrated by the arrows in FIG. 1. Pivotal movement of trigger 10 causes the tube housing to move in insulator housing 42 between a first rearward limit position (FIG. 1) wherein tube housing 106 is stopped by engagement with end cap 80 and a second forward limit position wherein the distal (forward) end of the tube housing is blocked by the tapered bore section 62 of the insulator housing.

Figures 15, 16:
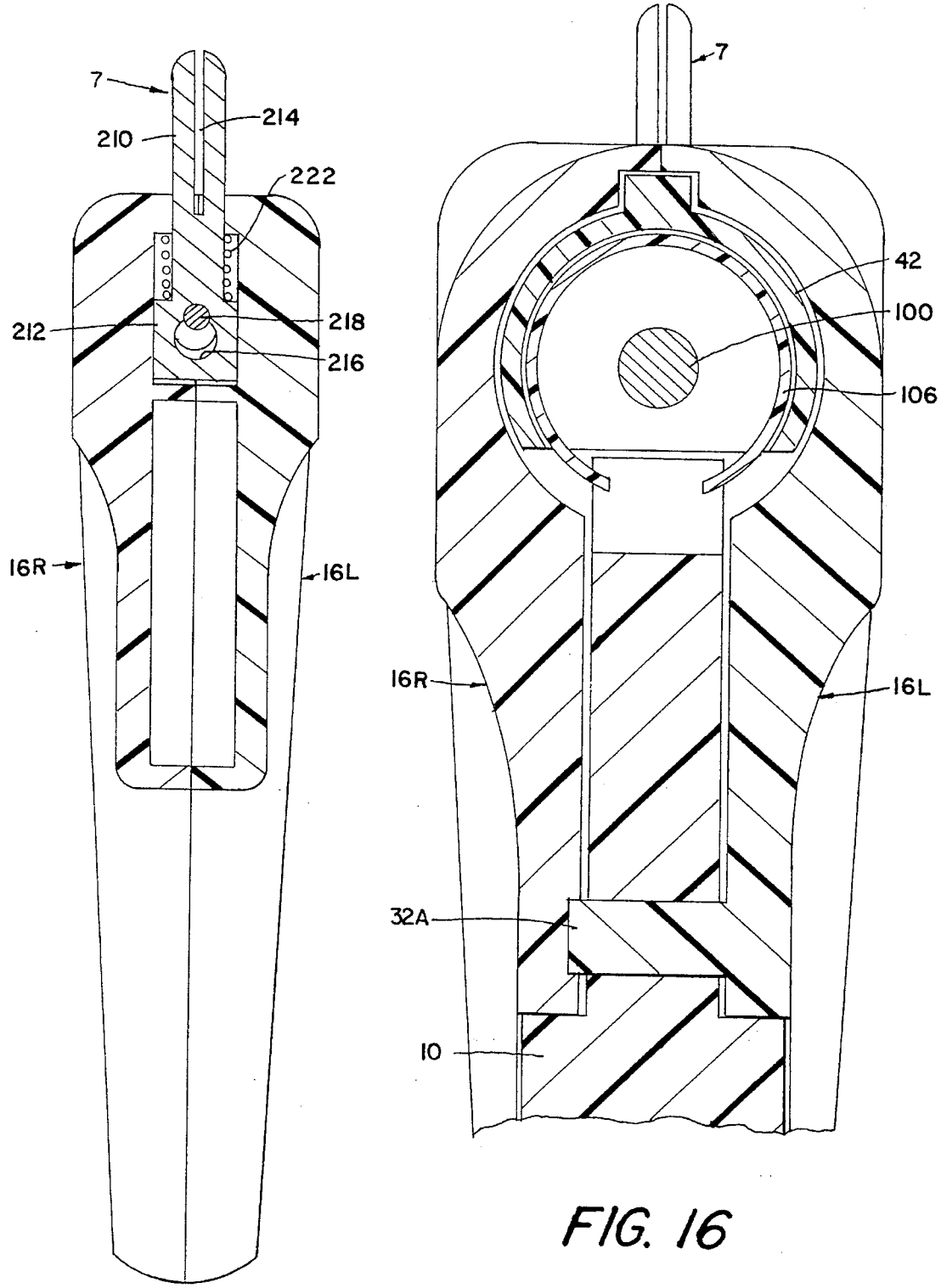
FIG. 15 is a cross-sectional view taken along line 15—15 of FIG. 1.
FIG. 16 is a cross-sectional view along line 16—16 of FIG. 1.

Referring now to FIGS. 10 and 15, the electrical terminal pin 7 is made of metal and comprises a round pin section 210 and an enlarged head section 212. Preferably pin section 210 is bifurcated as a result of a slot 214 so as to be compressible radially when coupled to a mating female connector. Head section 212 is generally round in cross-section except that it has diametrically opposed flat surfaces that mate with corresponding flat surface portions 25A and 25B (FIG. 2) of cavities 24L and 24R. Pin 7 also has a keyhole that extends perpendicular to its flat surfaces and comprises an enlarged section 216 and a reduced section 218. The latter section has a radius of curvature larger than that of section 140 but smaller than that of flange 142 and rounded end 136 of rod 100. The enlarged section 216 has a radius of curvature larger than the rounded end 136 of rod 100. A compression spring 222 surrounds pin section 210 in the hole formed by cavities 24L and 24R, being captivated between head section 212 and the shoulder formed by the intersection of cavities 26L and 26R with cavities 24L and 24R respectively. Spring 222 normally urges the terminal pin inwardly so as to have rod section 140 locked in keyhole section 218.

Referring now to FIGS. 13–15 and 22, tool head 6 can take various forms. In this preferred embodiment of the invention, it takes the form of a releasable scissors-type head.

In this connection it should be noted that it is preferred to provide the outer tube or sleeve 102 with a tubular sleeve-type bearing 230 (FIGS. 22 and 24) having a peripheral flange 232. Bearing 230 fits inside of and is bonded to tube 102, with the distal end of the tube engaging peripheral flange 232 as shown in FIG. 22. Bearing 230 may be made of TEFLON or some other commercially available material that has a relatively low coefficient of friction and the hardness required to withstand wear from repeated sliding contact with the tool head. The i.d. of bearing 230 is slightly larger than the o.d. of rod 100 and the o.d. of the body sections 250 of scissors blade members 246A and 246B hereinafter described.

Referring now to FIGS. 1, 22–24 and 28–30, tool head 6 is detachably secured to rod 100 so as to be locked against rotational or axial movement relative to the rod. For this purpose, rod 100 is provided with a tongue 240 having an enlarged head 242, with both the tongue and head having a pair of flat opposite surfaces 241 and 243 respectively. Tool head 6 is preferably formed of two identical scissors blade members 246A and 246B formed of a stainless steel with spring-like quality. Each blade member comprises a body section 250 that is semi-circular in cross-section, so as to have a flat face 252. In addition, each body section is notched and its flat face 252 is recessed as shown at 260 and 262 so that when the two faces are brought into confronting relation with one another, a bayonet slot 264 is formed as shown in FIG. 28 that is sized to mate with tongue 240 of rod 100 as shown in FIG. 22.

Still referring to FIGS. 22–25, blade members 246A and 246B are formed with spring arms 268 that are integral with body sections 250 and carry integral scissors blades 270. Arms 268 are formed so that in their normal state the scissors blades extend at an inclined angle to the longitudinal axes of body sections 250 (FIG. 28). An edge portion of each scissors blade is ground so as to provide a micropolished flat scissors face as shown at 272 that terminates in a sharp edge 274. Each scissors blade 270 is formed so that it is bent longitudinally as viewed in FIG. 30, so that its forward end or tip crosses the center axis of its associated body section 250. Accordingly, when the two scissors blade members are secured together at their flat faces 252 (FIG. 28) by welding or other means, so as to form bayonet slot 264, the scissors faces 272 are engaged with one another at their proximal or rear ends (FIG. 30), while their forward ends are separated (spaced apart) from one another (FIG. 28) but extend laterally across the center axis of the tool head, i.e., across the planes of faces 252. Consequently, if a radially-directed squeezing force is applied to blades 270 normal to faces 252 (as represented by the mutually-converging arrows in FIG. 28), the blades will be forced together, and when that occurs, the resulting interference caused by the fact that the blades cross one another (as seen in FIG. 30) will cause the blades to deflect back away from one another to an extent just sufficient to permit the sharp edges 274 to close on one another in a scissors-like cutting action.

As seen in FIG. 22, the scissors head 6 is sized so that its body sections 250 can slide within bearing sleeve 230. Also, blades 270 are sized so that they also can fit within and slide relative to bearing 230 when they are fully closed on one another.

Assembly of the tool involves several separately conducted subassembly procedures. The tool head 6 is assembled by welding or brazing blade members 246A and 246B together. In a separate procedure, helical gear 148 is mounted onto and secured to rod 100. Then tool head 6 is attached to rod 100 by inserting the rod's tongue 240 into bayonet slot 264.

Contemporaneously, or before or after the foregoing steps, tube 102 is affixed to tube housing 106, and tubular sheath 104 is affixed to insulator housing 42. Thereafter, rod 100, with tool head 6 attached, is inserted into the proximal (rear) end of tube housing 106 and forced forwardly so as to cause the scissors blade arms 268 to yield enough to allow scissors blades 270 to close on one another enough to permit the tool head to pass through tube 102 and bearing 230, and also to locate gear 148 in bore section 122. The diameter of bore section 122 is slightly oversized with respect to helical gear 148 so as to permit the gear to rotate therein. Thereafter, or before insertion of rod 100 into the tube housing, end cap 80 is mounted onto rod 100 as previously described. In this connection, it is to be noted that the semi-circular hole 90 in cap 80 is slightly larger than the diameter of rod section 138, while preferably the width of slot 88 in cap 80 is slightly smaller than the diameter of rod section 138, with the result that the end cap makes a snap fit with the drive rod. Molded cap 80 has flexibility that permits it to yield enough to allow rod 100 to be forced through slot 88 into hole 90.

Thereafter, the subassembly consisting of tube 102, tube housing 106, rod 100 with gear 148, and tool head 6, is slipped into the proximal (rear) end of insulator housing 42, with the internal rib 78 of the insulator housing being aligned and disposed in groove 116 and slot 114 of the tube housing. This step involves inserting tube 102 into sheath 104 so that blades 270 can project from the forward (distal) end of the sheath. When the subassembly consisting of tube 102, tube housing 106, etc., is inserted into the insulator housing, it is preferred that rod 100 be withdrawn enough in tube housing 106 (as viewed in FIGS. 10 and 22) to permit sleeve bearing 230 to surround scissors blades 270 and thereby apply a radially directed compression force that holds the blades in closed position. Having the scissors blades closed by bearing 230 facilitates insertion of the blades and tube into sheath 104. Thereafter rod 100 is shifted axially so as to permit end cap 80 to be seated in the rear end of the insulator housing, and end cap 80 is secured to that housing by a suitable cement or by ultrasonic welding as previously described. The internal rib 78 in insulator housing 42 cooperates with groove 116 and slot 114 to insure that the aperture 110 of the tube housing is in confronting alignment with the trigger member 10 when subsequently the resulting assembly is mounted to the handle assembly.

The foregoing combined subassemblies consisting of insulator housing 42 and its attached sheath 104, and tube housing 106 and its associated parts, is then combined with the handle assembly. The latter may be preassembled by starting with left handpiece 16L and first mounting trigger member 10 on pivot pin 32A. Simultaneously, or before or after the foregoing step, the rotational trigger 12 is placed onto the post 36A with its teeth engaged with helical gear 148, and the spring 166 attached thereto is subsequently attached to the post 34A. Then terminal pin 7, with compression spring 222 mounted thereon, is placed into cavities 24L and 26L, with spring 222 being compressed so as to provide a force urging pin 7 inwardly (downwardly as viewed in FIG. 10). Then the right handpiece 16R is placed over the foregoing assembly into engagement with the left handpiece 16L and the two handpieces are secured together by a suitable cement or by ultrasonic welding.

The handle assembly is attached to the assembly consisting of insulator housing 42 and tube housing 106, etc. by the simple expendent of inserting the insulating housing into the front end of the chamber formed by cavities 20L and 20R. When this is done, the rounded rear end of rod 100 engages the small keyhole section 218 and coacts with the edge of that keyhole section to cam pin 7 outwardly enough to align the enlarged keyhole section 216 with the rod, thereby allowing rod section 140 to be forced into alignment with the pin, whereupon spring 222 will force the pin inwardly again to lock rod 100 to the terminal pin, in turn locking the insulator housing to the handle assembly.

It is to be noted that when inserting the insulator housing into the handle assembly, the trigger 10 must be pulled back to its rear limit position as shown in FIG. 10 so as to permit the insulator housing 42 and cap 80 to clear the finger section 193 of the trigger, but the finger section 195 projects up far enough to intercept the lug. Thereafter, assuming that the insulator housing has been locked to the handle assembly, reverse movement of the trigger back to the position of FIG. 1 will cause finger section 193 to engage the lug and thereby move the tube housing rearwardly in the insulator housing.

As mentioned hereinabove, the elongate pivot hole 154 of the rotational trigger is sized so that spring 166 will hold it in a down and forward position (FIG. 10), in which position its teeth 156 do not protrude into the insulator housing far enough to intercept gear 148 and thus interfere with its axial movement when the tool assembly comprising the insulator housing and tube housing 106 is inserted into or pulled out of the handle assembly. To further facilitate detachment of the tool assembly from the handle assembly, the slot 114 in tube housing 106 is sized so as to provide clearance with trigger teeth 156 as the housing is inserted into or removed from the handle housing 16L, 16R.

Operation of the tool is as described hereinafter.

When trigger member 10 is in its forward limit position (FIG. 1), tube housing 106 and tube 102 are in their withdrawn or retracted position wherein bearing 230 terminates short of engagement with the blades 270 of tool head 6, with the result that the blades are in their separated or open position (FIGS. 1, 22 and 28). When trigger member 10 is pulled toward fixed handle 8 to its other limit position (FIG. 10), the pivotal connection between the trigger member and lug 112 of tube housing 106 causes the latter to be moved forward in housing 42, causing tube 102 to telescope forwardly and causing bearing member 230 to slip over and compress scissors blades 270 into closing position.

The angular orientation of scissors blades 230 relative to the handle assembly can be varied by manipulation of rotational trigger member 12. When trigger member 12 is pulled back, its gear teeth cause helical gear 148 to rotate, thereby rotating rod 100 and the tool head counterclockwise (as viewed in FIG. 17) relative to the fixed handle member 8. Because trigger member 12 has only a limited number of teeth, it must be retracted and then released several times in order to rotate the tool head 360°. By way of example but not limitation, the number of teeth on rotational trigger 12 and the number of teeth and the pitch thereof on helical gear 148 may be set so that trigger 12 must be pulled back and released approximately 8 times in order to achieve a 360° rotation of the tool head.

The preferred tool design described above offers a number of advantages. For one thing, the tool comprises several discrete lower tier subassemblies plus two discrete higher tier or major subassemblies, one of the major subassemblies being a multi-component handle assembly and the other comprising insulator housing 42, sheath 104, cap 80, tube housing 106, tube 102, rod 100, helical gear 148 and tool head 6, with the latter major subassembly being releasably secured to the handle assembly. Detachment of this higher tier or major subassembly from the handle assembly is achieved by pulling the terminal pin outwardly (upwardly as viewed in FIG. 10) so as to align the enlarged portion 216 of its keyhole with the rounded head 136 of rod 100, thereby allowing the handle assembly to be pulled free of rod 100. As a result, the major subassembly comprising insulator housing 42, sheath 104, cap 80, tube housing 106, tube 102, rod 100, helical gear 148 and tool head 6 can be replaced by a new and like substitute subassembly. In other words, the handle assembly is reusable with different substitute tool assemblies.

A second advantage resides in the fact that the scissors head shown in the drawings is removable from rod 100. A third advantage is that different tool heads may be used in place of the scissors head shown in the drawings. Thus, for example, the tool head may be a grasper head comprising a pair of jaws with confronting serrated surfaces that can be forced together by forward movement of tube 102 into grasping relation with tissue at a surgical site. The tool head also may comprise a combination grasper/cutter with one of the confronting faces of the two jaws having a cutting blade that is received in a notch in the other jaw. Another possibility is a tool head with cooperating members for holding a suture or a needle.

A fourth advantage resides in the fact that cap 80 need not be cemented to the insulator housing. Instead, as shown in dotted lines in FIG. 9, the cap could be provided with a peripheral groove 93 in its reduced section 92 and the insulator housing may be formed with an internal circumferentially-extending rib (not shown) sized to make a snap fit in groove 93, thereby permitting the cap to be releasably interlocked with the insulator housing. If such arrangement is adopted, the cap may be easily detached from the insulator housing out of connection with rod 100, thereby permitting the rod and its attached tool head to be withdrawn rearwardly out of tube 102 and insulator housing 42. This alternative embodiment facilitates removal and replacement of the subassembly consisting of rod 100, helical gear 148 and the tool head 6, or simply of replacement of the tool head 6.

A further advantage resides in the fact that the rotational trigger permits the surgeon to rotate the scissors blades relative to the handle assembly by a precise amount, thereby avoiding the need to rotate the handle assembly to achieve a particular cutting orientation of the scissors blades. The latter advantage is beneficial to the surgeon from the standpoint of comfort and ease of manipulation and ease of operation.

Still another advantage resides in the fact that bearing sleeve 230 applies a like force to each of the two scissors arms 268, with the force being distributed evenly about the circumference of the curved outer surfaces of scissors arms 268. Bearing 230 coacts with scissors arms 268 to urge blades toward one another as they are forced to close on one another.

A particularly significant advantage of this invention resides in the fact that rod 100 is stationary and surrounding tube 102 is reciprocated by manipulation of trigger member 10. This invention recognizes that surgeons need a point of reference in order to determine if and when they are moving a surgical scissors relative to the surgical site. In the absence of sheath 104, movement of outer tube 102 as seen by the surgeon might have a tendency to confuse the surgeon into believing that the tool is moving axially relative to the patient. The provision of outer sheath 104 eliminates the possibility of such confusion. Since sheath 104 is at least coextensive with tube 102 (and preferably projects slightly forward of tube 102 even when the tube is moved to its forwardmost position relative to rod 100) and hence conceals any axial movement of that tube relative to handle assembly 2, manipulation of handle members 8 and 10 causing the jaws to open and close is accomplished without the surgeon realizing that there is actual axial movement of tube 102. Instead, the surgeon sees that sheath 104 is stationary, with the result that the surgeon is free to concentrate his attention on the actual position of the scissors blades 230 (the latter do not appear to move toward and away from the patient when the jaws are opened or closed, unless the surgeon actually moves the tool relative to the patient).

Still another significant advantage is that the tool described above is adapted to conduct monopolar cauterization, but also may be used without being electrified. If the tool is to be made for non-cauterization uses, pin 7 need not be an electrically-conductive element and instead may function simply as a locking device for rod 100 as hereinabove described.

Other advantages will be obvious to persons skilled in the art.

MODIFICATIONS OF THE INVENTION

Persons skilled in the art will also appreciate that the invention is susceptible to various modifications. Thus, as noted above, various forms of tool heads may be used in practicing the invention. Also the tool head 6 may be permanently secured to the rod 100. Additionally, the manner of connecting various components may be varied. Thus, the proximal (rear) end of tube 102 may be externally threaded to mate with an internal thread formed in the bore section 128 of tube housing 106. Also, the insulator sheath 104 may be formed of a material which is sufficiently rigid to permit it to be formed with an external screw thread, thereby permitting it to mate with a cooperating internal thread formed in bore 66 of insulator housing 42. A further possible modification resides in the fact that a different tool head may be attached to the operating rod 100. For example, the tool head may comprise a grasper arrangement, e.g., a grasper arrangement as disclosed in U.S. Pat. No. 3,404,677, issued Oct. 8, 1968 to H. A. Springer for "Biopsy And Tissue Removing Device".

FIG. 31 shows another modification of the invention wherein a compression spring 290 is mounted on rod 100 between the forward end of tube housing 106 and the tapered bore section 162 of insulator housing 42. Spring 290 urges tube housing 106 rearwardly in the insulator housing so that it is intercepted by cap 80, in which position the tube housing holds trigger member 10 in its forward (open) position as shown in FIG. 1.

Still another possible modification is to provide a different form of pivotal connection between trigger 10 and tube housing 106. Thus, for example, tube housing 106 could be provided with a radially-extending external projection having a pivot hole, and trigger member 10 could be provided with a pivot hole designed to mate with the pivot hole on the external extension of the tube housing, with a separate pivot pin being inserted into the mating pivot holes and secured in place so as to pivotally connect the trigger to the extension on the tube housing.

Still another possible modification involves connection of the electrical terminal pin to drive rod 100. It is envisioned that the proximal (rear) end of rod 100 may be provided with a threaded axially-extending hole, and the terminal pin may be attached to rod 100 by providing the terminal pin with an externally-threaded front end that screws into the tapped hole in the end of the rod. In such event, the terminal pin may extend parallel rather than at a right angle to the longitudinal axis of the insulator housing. A further possibility is to use a separate electrically conductive screw to secure the conductive terminal pin to the threaded axially extending hole in the rear end of rod 100.

Another contemplated modification is to provide a scissors head wherein the two blade members 246A and 246B are not permanently secured together by welding or brazing but instead are releasably or permanently affixed in an adapter member (not shown) that is designed to mate with the forward end of rod 100. The adapter may be releasably or permanently cocupled to the rod.

Figure 32:
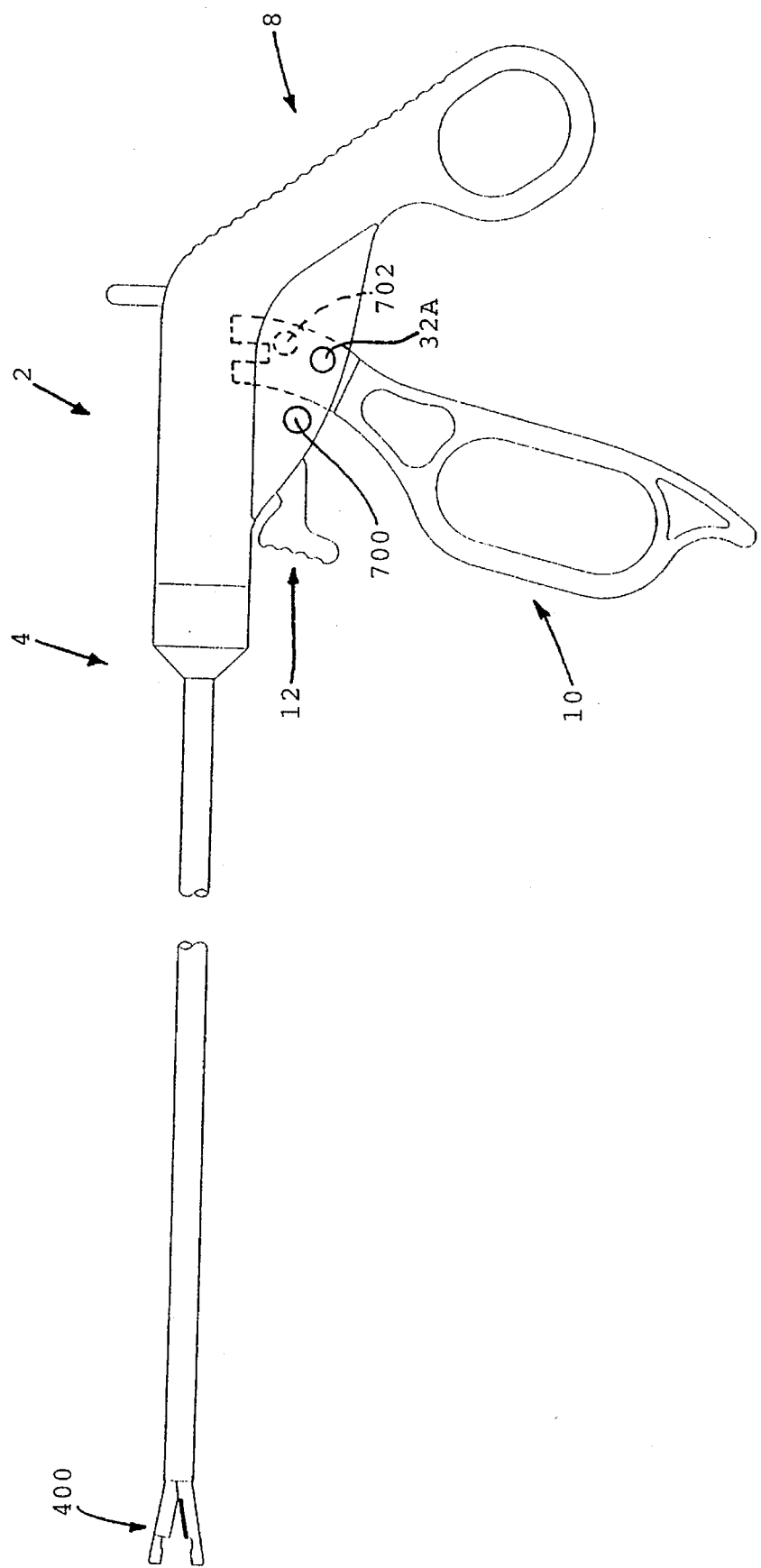
FIG. 32 is a side elevational view of a surgical instrument formed in accordance with the present invention having a novel tool head designed to facilitate suture throw rundown toward a surgical site.

In yet another contemplated modification, and looking now at FIG. 32, a novel tool head 400 is shown coupled to rod 100 for use in tying off suture ends extending away from a surgical site.

Novel tool head 400 is shown in greater detail in FIGS. 33–36. Novel tool head 400 generally comprises means for running suture throws toward a surgical site so as to form a knot and means for severing the suture ends extending away from the knot. More particularly, novel tool head 400 is preferably formed out of two scissor members 500 (see FIGS. 33–39) and 600 (see FIGS. 33–36 and 40–42) which preferably are made of a suitable metal such as stainless steel.

Looking now at FIGS. 33–39, first scissor member 500 comprises a rod engaging portion 502, a sleeve engaging portion 504, an elastically flexible portion 506, a substantially rigid blade portion 508, and a suture throw rundown element 510.

Looking now at FIGS. 37–39, rod engaging portion 502 has a semi-cylindrical cross-section comprising a flat inner surface 512 and a semi-circular outer surface 514. A distal portion 516 is disposed between and connects rod engaging portion 502 and sleeve engaging portion 504. Distal portion 516 has a semi-cylindrical cross-section and is sized so as to have a semi-circular outer surface 518 that is smaller in diameter than the diameter of rod engaging portion 502.

Sleeve engaging portion 504 also has a semi-cylindrical cross-section, It comprises a flat inner surface 520 and a semi-circular outer surface 522. Flat inner surface 520 is substantially coplanar with flat inner surface 512 of rod engaging portion 502. Semi-circular outer surface 522 has a diameter that is larger than the diameter of rod engaging portion 502.

Figure 33:
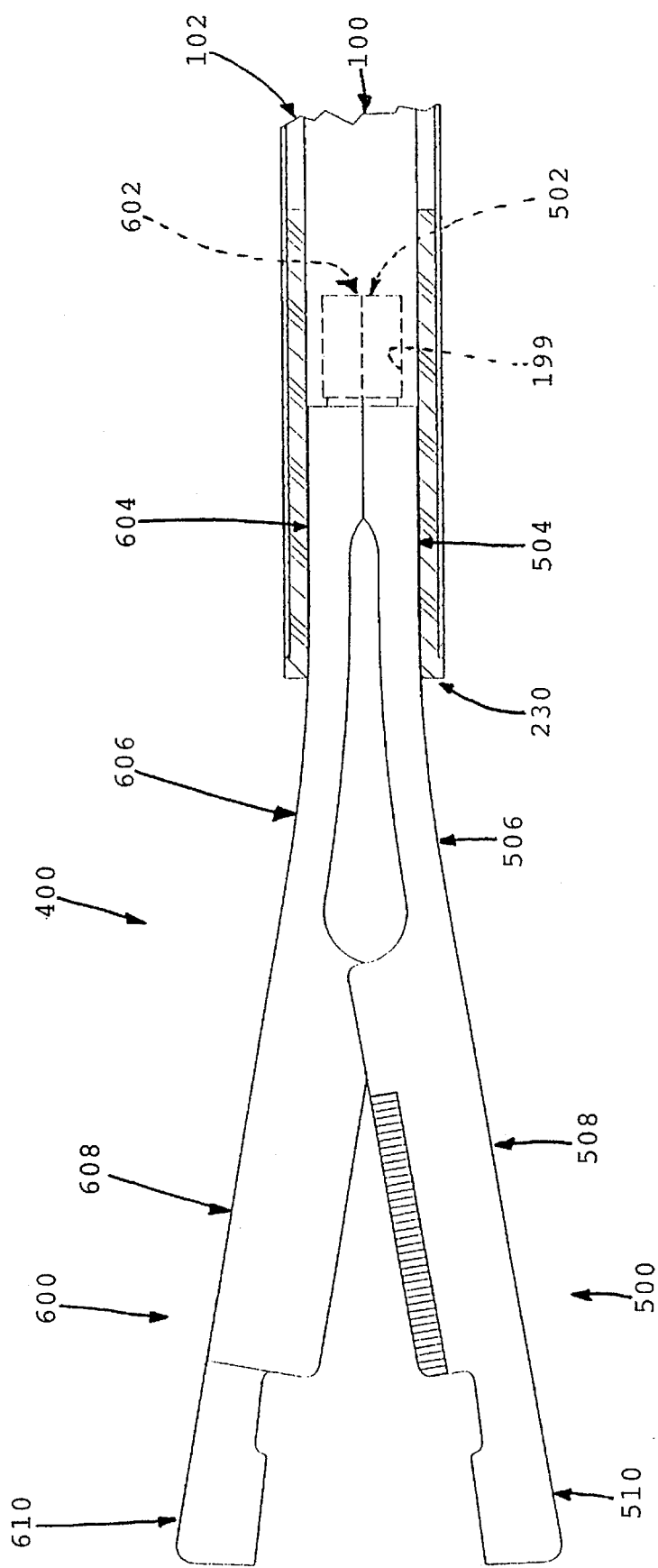
FIG. 33 is an enlarged side view, partially cut away and partially in section, showing the novel tool head of FIG. 32 in its open position.

Elastically flexible portion 506 extends from and is connected to the distal end of sleeve engaging portion 504. It is normally outwardly and distally curved relative to sleeve engaging portion 504, as seen in FIG. 33. Elastically flexible portion 506 comprises a semi-cylindrical cross-section that is smaller than the cross-section of sleeve engaging portion 504. Elastically flexible portion 506 connects sleeve engaging portion 504 to rigid blade portion 508.

Rigid blade portion 508 comprises a substantially semi-cylindrical shape, so as to have a semi-circular outer surface 524 and a flat inner surface 526. Semi-circular outer surface 524 further includes a substantially flattened portion 528 defining a cutting edge 530. Cutting edge 530 is adapted for bearing against a similar cutting edge 630 located on second scissor member 600 as will hereinafter be described in further detail.

A connector portion 532 extends distally from rigid blade portion 508 and connects the latter to suture throw rundown element 510. Connector portion 532 has a frustoconical shape adapted to interconnect the distal portion of rigid blade portion 508 with the proximal portion of suture throw rundown element 510.

Suture throw rundown element 510 comprises a semi-frustoconical wall 534 having a curved inner surface 536 and a curved outer surface 538. Wall 534 has a cylindrical bore 540 that extends between inner surface 536 and outer surface 538. Bore 540 is disposed at an angle relative to inner and outer surfaces 536 and 538 and is spaced from the distal end 542 of first scissor member 500.

Second scissor member 600 (see FIGS. 33-36 and 40-42) is essentially identical to first scissor member 500, except as hereinafter described in detail. More particularly, second member 600 comprises a rod engaging portion 602, a sleeve engaging portion 604, an elastically flexible portion 606, a substantially rigid blade portion 608, and a suture throw rundown element 610.

Looking now at FIGS. 40-42, rod engaging portion 602 has a semi-cylindrical cross-section comprising a flat inner surface 612 and a semi-circular outer surface 614. A distal portion 616 is disposed between and connects rod engaging portion 602 and sleeve engaging portion 604. Distal portion 616 has a semi-cylindrical cross-section and is sized so as to have a semi-circular outer surface 618 that is smaller in diameter than the diameter of rod engaging portion 602.

Sleeve engaging portion 604 also has a semi-cylindrical cross-section. It comprises a flat inner surface 620 and a semi-circular outer surface 622. Flat inner surface 620 is substantially coplanar with flat inner surface 612 of rod engaging portion 602. Semi-circular outer surface 622 has a diameter that is larger than the diameter of rod engaging portion 602.

Elastically flexible portion 606 extends from and is interconnected to the distal end of sleeve engaging portion 604. It is normally outwardly and distally curved relative to sleeve engaging portion 604, as shown in FIG. 33. Elastically flexible portion 606 comprises a semi-cylindrical cross-section that is smaller than the cross-section of sleeve engaging portion 604. Elastically flexible portion 606 connects sleeve engaging portion 604 to rigid blade portion 608.

Rigid blade portion 608 comprises a substantially semi-cylindrical shape, so as to have a semi-circular outer surface 624 and a flat inner surface 626. Semi-circular outer surface 624 further includes a substantially flattened portion 628 defining a cutting edge 630. Cutting edge 630 is adapted for bearing against the similar cutting edge 530 located on first scissor member 500 as previously described.

A connector portion 632 extends distally from rigid blade portion 608 and connects the latter to suture throw rundown element 610. Connector portion 632 has a frustoconical shape adapted to interconnect the distal portion of rigid blade portion 608 with the proximal portion of suture throw rundown element 610.

Suture throw rundown element 610 comprises a semi-frustoconical wall 634 having a curved inner surface 636 and a curved outer surface 638.

Suture throw rundown element 610 differs from suture throw rundown element 510 in that a slot 650 and a bore 652 are substituted for the bore 540.

More particularly, a slot 650 extends into a portion of the suture throw rundown element's distal end 642. Slot 650 intersects a bore 652 that extends through sidewall 634 of suture throw rundown element 610. Thus, outer surface 638 of suture throw rundown element 610 communicates with inner surface 636 via slot 650 and bore 652. Slot 650 and bore 652 are aligned with one another lengthwise of rundown element 610. In addition, tool head 400 is constructed so that bore 652 of suture throw rundown element 610 will be generally aligned diametrically with bore 540 of suture throw rundown element 510 when the two suture throw rundown elements abut one another as shown in FIGS. 35 and 36. Suture throw rundown element 610 is bevelled on its inner surface around hole 652 and along slot 650, as shown at 654.

Figure 34:
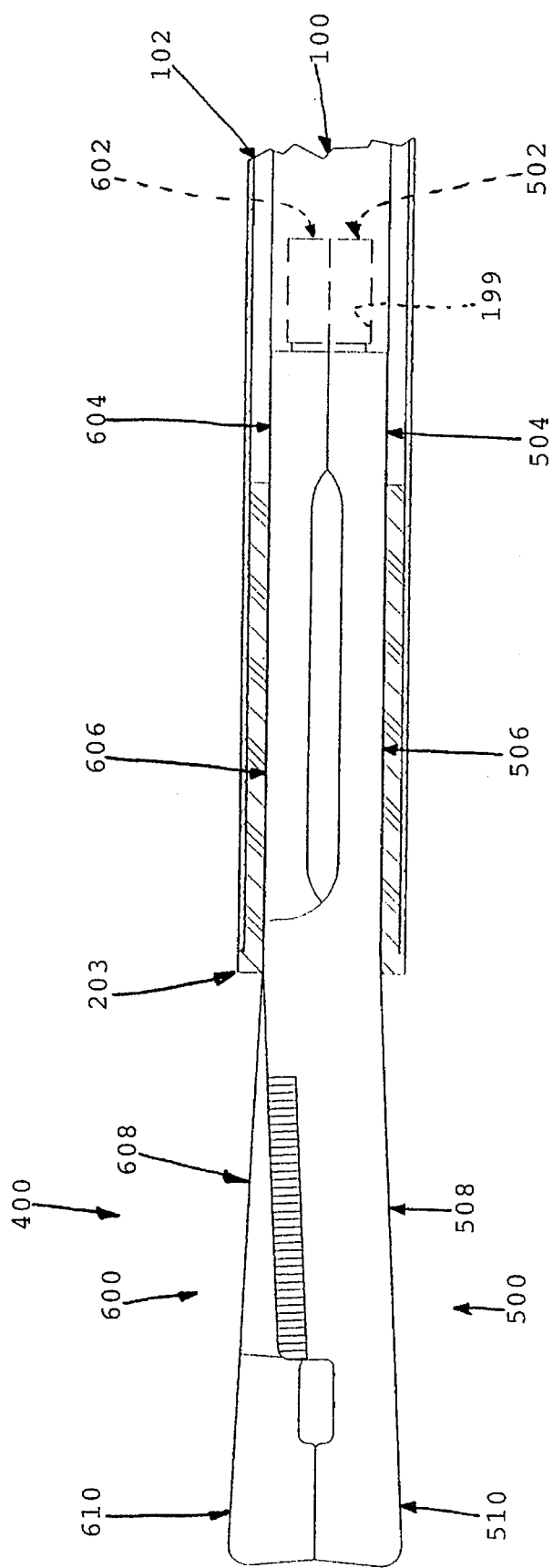
FIG. 34 is an enlarged side view, partially cut away and partially in section, showing the novel tool head of FIG. 32 in its closed position.

Looking next at FIGS. 34-36, when tube 102 is in its second extended position, the first and second scissor members 500 and 600 will be located substantially adjacent to one another such that the inner surfaces 526 and 626 of their respective rigid blade portions 508 and 608 will engage one another. In addition, the suture throw rundown elements 510 and 610 will substantially abut one another so as to form a generally cylindrical axially-extending cavity 402 (FIG. 35) defined by the union of curved inner surface 536 of suture throw rundown element 510 and the curved inner surface 636 of suture throw rundown element 610.

Tool head 400 is assembled to rod 100 as follows. Rod 100 comprises a distally facing cavity 199 (FIGS. 33 and 34) located at its distal end. Cavity 199 corresponds in size and shape to the size and shape of rod engaging portions 502 and 602 when those portions are in aligned, abutting relationship with one another, as shown in FIGS. 33 and 34. Also, when rod engaging portions 502 and 602 are in aligned, abutting relationship with one another, surfaces 512 and 612 are also in abutting relationship. Thus, first scissor member 500 and second scissor member 600 may be coupled to rod 100 by locating their rod engaging portions 502 and 602 within rod cavity 199 at the distal end of rod 100, and thereafter securing them in place by welding or other suitable attachment means. They also may be attached by a press fit.

As a consequence of the foregoing attachment operation, sleeve engaging portions 504 and 604 will also be aligned with one another such that flat surfaces 520 and 620 abut one another. In this configuration, sleeve engaging portions 504 and 604 will together define a generally cylindrical structure. Outer surfaces 522 and 622 of the aligned sleeve engaging portions 504 and 604 slidably engage the tubular sleeve-type bearing 230 (see FIGS. 33 and 34) which is located adjacent to the inner proximal end of tube 102, as previously disclosed.

Accordingly, when tube 102 is moved from its first retracted position (FIG. 33) to its second extended position (FIGS. 34 and 35), tubular sleeve-type bearing 230 will first slidingly engage outer surfaces 522 and 622 of first and second scissor members 500 and 600. As tube 102 continues to move distally, tubular sleeve-type bearing 230 will then radially compress elastically flexible portions 506 and 606 toward one another, so as to cause cutting edges 530 and 630 to close on one another in a scissors action. Once tube 102 is in its fully extended second position (see FIG. 35), suture throw rundown elements 510 and 610 combine to form a unified assembly. When tube 102 is thereafter moved from its second extended position (FIGS. 34 and 35) to its first retracted position (FIG. 33), first and second scissor members 500 and 600 will automatically return to the position shown in FIG. 33.

If desired, a locking pin 700 (see FIG. 32) may be provided in handle 8 to releasably engage a bore 702 formed in trigger 10 so as to releasably hold novel tool head 400 in its closed position when desired.

Figure 45:
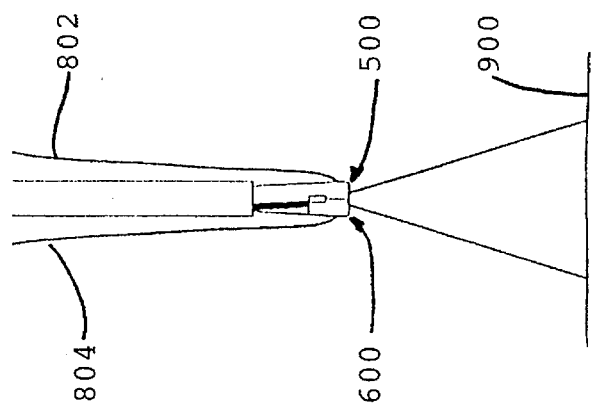
FIG. 45 is a view similar to that of FIG. 44, but showing the other suture end threaded through the other one of the tool head members, and with the two tool head members being shown in their closed position.
Figure 44:
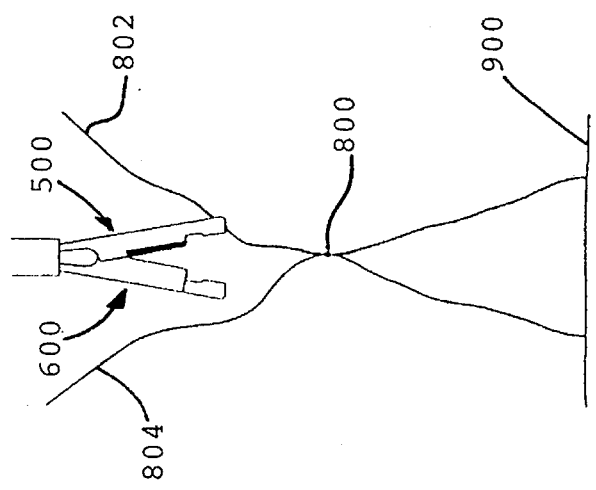
FIG. 44 is a view similar to that of FIG. 43, but showing one of the suture ends threaded through one of the tool head members.
Figure 43:
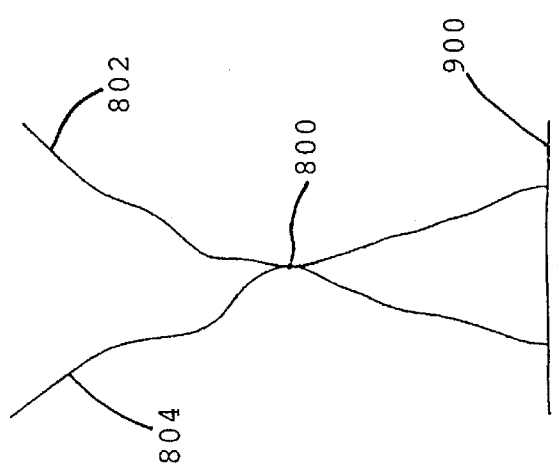
FIG. 43 is an illustrative view showing two suture ends extending away from a surgical site, with a surgical throw being formed in the suture ends at a location spaced from the surgical site.

Referring now to FIGS. 43–49, one preferred method for tying off suture with the apparatus of the present invention comprises the steps of:

(1) forming a suture throw 800 in the suture ends 802 and 804 extending away from tissue 900 which is located at a surgical site (FIG. 43);

(2) with the surgical instrument's tube 102 in its first retracted position, threading suture end 802 through bore 540 in first scissor member 500 (FIG. 44);

(3) sliding the other suture end 804 through the second scissor member's slot 650 and into its bore 652, and moving the surgical instrument's tube 102 to its second extended position so as move the scissor members into their closed position (FIG. 45);

(4) while holding suture ends 802 and 804 taut, running suture throw 800 down the lengths of suture toward tissue 900 by moving the surgical instrument toward the tissue (FIG. 46);

(5) moving the surgical instrument's tube 102 to its first retracted position while holding the tool stationary relative to the surgical site, thereby allowing the first and second scissor members 500 and 600 to move elastically away from each other and to pull the suture throw 800 tight at tissue 900 (FIG. 47);

(6) disengaging suture ends 802 and 804 from the surgical instrument by pulling the instrument back from the surgical site;

(7) with the surgical instrument's tube 102 in its first retracted position so that scissor members 600 and 500 are in open position, positioning the surgical instrument adjacent to the suture ends 802 and 804 (FIG. 48); and (8) moving tube 102 from its first retracted position to its second extended position, thereby causing cutting blades 530 and 630 to be brought against one another and thereby sever the suture ends 802 and 804 with a scissor-type action (see FIG. 49).

In the usual course of practicing the invention, steps 1–6 may be repeated several times before step (7) to form a desired knot adjacent tissue 900.

Since still other changes may be made in the apparatus without departing from the scope of the invention herein involved, it is intended that all matter contained in the above description or shown in the drawings shall be interpreted in an illustrative and not in a limiting sense.

What is claimed is:

1. A surgical instrument comprising:

a handle assembly;

a tool head comprising first and second cooperating tool members movable between a first position wherein said tool members are spaced from one another and a second position wherein said tool members are proximate to one another, said first and second tool members comprising first means for running surgical suture throws toward a surgical site to form a knot, and second means for severing excess lengths of suture adjacent to said knot; and drive means attached to said handle assembly and connected to said tool head for moving said first and second cooperating tool members between said first position and said second position;

wherein said first means comprise a substantially semi-cylindrical portion on each of said first and second cooperating tool members, said substantially cylindrical portions being configured to substantially abut one another in mating relationship when said first and second tool members are located in said second position so as to form a cavity having an open distal end and a sidewall, said sidewall comprising a first bore extending at an angle therethrough and a second bore extending substantially radially through an opposing portion of said sidewall, said second bore being connected to the distal end of said cavity sidewall by a slot, and said first bore, said second bore, and said slot all being substantially aligned.

2. A surgical instrument according to claim 1 wherein said handle assembly is adapted to operate said drive means.

3. A surgical instrument according to claim 1 wherein said drive means comprises a discrete subassembly that is detachable as a unit from said handle assembly.

4. A surgical instrument according to claim 3 wherein said discrete subassembly is releasably locked to said handle assembly by a spring-biased locking member.

5. A surgical instrument according to claim 1 further including rotating means for rotating said tool head relative to said handle assembly.

6. A surgical instrument according to claim 1 wherein said drive means comprises an elongate rod, a hollow tube surrounding said rod, means for securing one end of said rod to said handle assembly, means for securing said tool head to the opposite end of said rod, support means for slidably supporting said tube for sliding axial movement relative to said rod, said support means comprising a first housing releasably secured to said handle assembly, said first housing defining an elongate chamber, and a second housing slidably mounted in said elongate chamber, said tube being secured to and movable with said second housing, and said rod extending through said second housing and being secured to said first housing, said rod and said tube cooperating to move said first and second cooperating tool members in response to axial movement of said tube relative to said rod.

7. A surgical instrument according to claim 6 wherein said handle assembly comprises a hollow body portion with said first housing extending therein.

8. A surgical instrument according to claim 1 wherein said second means comprises a cutting blades on each of said first and second tool members, said cutting blades being arranged to engage one another when said first and second tool members are moved to said second position.

9. A surgical instrument comprising;

a handle assembly;

a tool head comprising first and second cooperating tool members movable between a first position wherein said tool members are spaced from one another and a second position wherein said tool members are proximate to one another, said first and second tool members comprising first means for running, surgical suture throws toward a surgical site to form a knot, and second means for severing excess lengths of suture adjacent to said knot; and drive means attached to said handle assembly and connected to said tool head for moving said first and second cooperating tool members between said first position and said second position;

wherein said first means comprise a substantially semi-cylindrical portion located distally of said second means on each of said first and second cooperating tool members, said substantially cylindrical portions being configured to substantially abut one another in mating relationship when said first and second tool members are located in said second position so as to form a cavity having an open distal end and a sidewall, said sidewall comprising a first bore extending at an angle therethrough and a second bore extending substantially radially through an opposing portion of said sidewall, said second bore being connected to the distal end of said cavity sidewall by a slot, and said first bore, said second bore, and said slot all being substantially aligned; and wherein said second means comprises a cutting blade on each of said first and second tool members, said cutting blades being arranged to engage one another when said first and second tool members are moved to said second position.

10. A surgical instrument comprising a handle and trigger assembly and an operating tool assembly separably connected to said handle and trigger assembly;

said handle and trigger assembly comprising a handle housing having a chamber therein and a trigger member pivotally mounted to said handle housing;.

said operating tool comprising at one end thereof a tool head including first means for running surgical suture throws toward a surgical site to form a knot and second means for severing excess suture lengths adjacent to said knot, and at the opposite end thereof a tubular housing that extends into said chamber;

said handle and trigger assembly having locking means engaged with said operating tool assembly for releasably locking said tubular housing to said handle housing;

said operating tool assembly further comprising a mechanism for moving portions of said first means for running suture throws and said second means for severing excess suture toward and away from one another, said mechanism including movable means in said tubular housing engaged and movable by said trigger member for causing said mechanism to move said portions of said first means for running suture throws and said second means for severing excess suture toward and way from one another in response pivotal movement of said trigger assembly;

wherein said mechanism includes first and second cooperating tool members, and wherein said second means comprises opposing cutting blades on said first and second cooperating tool members, and said first means comprises a substantially semi-frustoconical portion located distally of said cutting blade on each of said first and second cooperating tool members, said substantially frustoconical portions being configured to substantially abut one another in mating relationship when said first and second cooperating tool members are located in [their second] a closed position so as to form a distally facing open cylindrical cavity having an open distal end and a sidewall, [and] said sidewall defining a first bore extending therethrough and an opposing second bore extending substantially radially therethrough, said second bore being connected to said distal end of said cavity sidewall by a longitudinal slot, and said first bore, said second bore and said slot all being substantially aligned.

11. A method for forming a surgical knot in lengths of suture extending from a surgical site, said method comprising the steps of:

(a) providing a surgical instrument comprising a tool head having first and second cooperating tool members movable between a first open position wherein said tool members are spaced from one another and a second closed position wherein said tool members are proximate to one another, said first and second tool members comprising first means for running surgical suture throws toward the surgical site and second means for severing excess lengths of suture adjacent to said knot; said first means comprising a substantially semi-cylindrical portion on each of said tool members, configured to abut each other in mating relationship in said second position so as to form a cavity having an open distal end and a sidewall, said sidewall having a bore extending therethrough and a slot extending therethrough, said slot having an open end at said distal end of said cavity and a closed end opposed to said bore; and drive means for moving said first and second cooperating tool members between said first open position and said second closed position;

(b) forming a surgical throw in lengths of suture extending from the surgical site;

(c) with said tool members in said first open position, capturing one of said lengths of suture in said bore disposed in said first tool member;

(d) moving said tool members to said second closed position and capturing the other length of said suture in said slot disposed in said second tool member;

(e) while holding said lengths of suture taut, running said surgical throw toward the surgical site with said surgical instrument;

(f) moving said tool members to said first open position, thereby allowing said first and second members to pull said surgical throw taut;

(g) withdrawing said surgical instrument from the vicinity of the surgical site to permit said other length of said suture to drop from said slot; and (h) disengaging said one of said lengths of suture from said first tool member by drawing said one length of suture through said bore.

12. The method of claim 11 further including the step of releasably locking said tool members in said second closed position during the running of said surgical suture throws along said lengths of suture extending from said surgical site.

13. A surgical instrument comprising:

a drive means disposed in a tube;

first and second tool members fixed, respectively, at one end to said drive means and biased away from each other and movable by said drive means between a first position in which said tool members are extended from said tube and biased away from each other and a second position in which said tool members are in part drawn into said tube and thereby forced toward and proximate each other;

a first head portion disposed at a distal end of said first tool member, said first head portion having a bore therethrough for receiving and retaining a first suture strand such that the first suture strand is slidable lengthwise through said bore, said bore being spaced from a distal end of said first head portion; and a second head portion disposed at a distal end of said second tool member, said second head portion having a slot therethrough with an open end at a distal end of said second head portion and a closed end opposed to said bore for receiving and retaining a second suture strand such that the second suture strand is receivable by said slot generally widthwise of said second suture strand through said open end of said slot, and said second suture strand is slidable lengthwise through said slot;

whereby said first and second tool members in said second position are adapted for running said suture strands toward a surgical site, and are movable by said drive means from said second position to said first position to pull said suture strands taut to form a knot.

14. The instrument in accordance with claim 13 wherein said slot at said closed end thereof is provided with an enlarged portion opposed to said bore.

15. The instrument in accordance with claim 13 wherein each of said tool members is provided with blade means for cutting the suture strands.

16. The instrument in accordance with claim 13 wherein said first head portion is devoid of an opening therethrough, other than said bore, and said second head portion is devoid of an opening therethrough, other than said slot.

17. The instrument in accordance with claim 16 wherein said first and second head portions each comprise a substantially semi-cylindrical portion configured such that said first and second head portions abut each other in mating relationship when said head portions are in said second position, to form a cavity having an open distal end and a sidewall, said sidewall having therethrough said bore and said slot.

18. The instrument in accordance with claim 17 wherein said bore extends through said sidewall at an angle to an axis of said head portion when in said mating relationship.

19. The instrument in accordance with claim 17 wherein said bore extends through said sidewall at an angle to an axis of said head portions when in said mating relationship and said enlarged portion of said slot extends substantially radially through said sidewall.

20. A surgical instrument comprising:

first and second tool members fixed to a drive assembly and movable thereby;

a first head portion disposed at a distal end of said first tool member, said first head portion having a bore therethrough for receiving and retaining a first suture strand such that the first suture strand is slidable lengthwise through said bore, said bore being spaced from a distal end of said first head portion; and a second head portion disposed at a distal end of said second tool member, said second head portion having a slot therethrough with an open end at a distal end of said second head portion and a closed end opposed to said bore for receiving and retaining a second suture strand such that the second suture strand is receivable by said slot generally widthwise of said second suture strand through said open end of said slot, and said second suture strand is slidable lengthwise through said slot.

21. The instrument in accordance with claim 20 wherein said slot at said closed end thereof is provided with an enlarged portion opposed to said bore.

22. The instrument in accordance with claim 20 wherein said first head portion is devoid of an opening therethrough, other than said bore, and said second head portion is devoid of an opening therethrough, other than said slot.

23. The instrument in accordance with claim 22 wherein said first and second head portions each comprise a substantially semi-cylindrical portion configured such that said first and second head portions abut each other in mating relationship when said head portions are in said second position, to form a cavity having an open distal end and a sidewall, said sidewall having therethrough said bore and said slot.

24. The instrument in accordance with claim 23 wherein said bore extends through said sidewall at an angle to an axis of said head portion when in said mating relationship.

25. The instrument in accordance with claim 21 wherein said bore extends through said sidewall at an angle to an axis of said head portions when in said mating relationship and said enlarged portion of said slot extends substantially radially through said sidewall.

26. The instrument in accordance with claim 20 wherein blade means are disposed on each of said tool members.

* * * * *